US007060249B2

(12) United States Patent
Ganetzky et al.

(10) Patent No.: US 7,060,249 B2
(45) Date of Patent: Jun. 13, 2006

(54) NEURODEGENERATION MUTANTS, METHOD FOR IDENTIFYING SAME, AND METHOD FOR SCREENING NEUROPROTECTIVE AGENTS

(75) Inventors: Barry S. Ganetzky, Madison, WI (US); Michael J. Palladino, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 456 days.

(21) Appl. No.: 10/154,086

(22) Filed: May 22, 2002

(65) Prior Publication Data

US 2003/0226156 A1    Dec. 4, 2003

(51) Int. Cl.
*A61K 49/00* (2006.01)
*A01K 67/033* (2006.01)

(52) U.S. Cl. ............................................ 424/9.2; 800/8
(58) Field of Classification Search ................. 424/9.2; 800/8

See application file for complete search history.

(56) References Cited

U.S. PATENT DOCUMENTS

2004/0177388 A1* 9/2004 Botas et al. .................... 800/8

FOREIGN PATENT DOCUMENTS

WO    WO 02/058626 A2 *  8/2002

OTHER PUBLICATIONS

Steffan et al., "Histone deacetylase inhibitors arrest polyglutamine-dependent neurodegeneration in Drosophila," Nature 413:739-743, Oct. 18, 2001.*
Min et al., "Preventing neurodegeneration in the Drosophila mutant bubblegum," Science, 284: 1985-1988, Jun. 18, 1999.*
Arguello JM, Whitis J, Cheung MC, Lingrel JB. Functional role of oxygen-containing residues in the fifth transmembrane segment of the Na,K-ATPase alpha subunit. Arch Biochem Biophys. Apr. 15, 1999;364(2):254-63.
Arguello JM, Whitis J, Lingrel JB. Alanine scanning mutagenesis of oxygen-containing amino acids in the transmembrane region of the Na,K-ATPase. Arch Biochem Biophys. Jul. 15, 1999;367(2):341-7.
Beal, M. F., Hyman, B. T., and Koroshetz, W. (1993). Do defects in mitochondrial energy metabolism underlie the pathology of neurodegenerative diseases?, Trends Neurosci 16, 125-31.
Bignami A, Palladini G. Experimentally produced cerebral status spongiosus and continuous pseudorhythmic electroencephalographic discharges with a membrane-ATPase inhibitor in the rat. Nature. Jan. 22, 1966;209(21):413-4.

Bonini NM. Drosophila as a genetic approach to human neurodegenerative disease. Parkinsonism Relat Disord. Jul. 2001;7(3):171-175.
Buchanan RL, Benzer S. Defective glia in the Drosophila brain degeneration mutant drop-dead. Neuron. May 1993;10(5):839-50.
Burgess DL, Jones JM, Meisler MH, Noebels JL. Mutation of the Ca2+ channel beta subunit gene Cchb4 is associated with ataxia and seizures in the lethargic (lh) mouse. Cell. Feb. 7, 1997;88(3):385-92.
Calandriello L, Curini R, Pennisi EM, Palladini G. Spongy state (status spongiosus) and inhibition of Na,K-ATPase: a pathogenetic theory. Med Hypotheses. Mar. 1995;44(3):173-8.
Coombe, P. E., and M. Heisenberg, 1986 The structural brain mutant Vacuolar medulla of Drosophila melanogaster with specific behavioral defects and cell degeneration in the adult. J Neurogenet 3: 135-158.
Davis MW, Somerville D, Lee RY, Lockery S, Avery L, Fambrough DM. Mutations in the Caenorhabditis elegans Na,K-ATPase alpha-subunit gene, eat-6, disrupt excitable cell function. J Neurosci. Dec. 1995;15(12):8408-18.
Elkins T, Ganetzky B, Wu CF. A Drosophila mutation that eliminates a calcium-dependent potassium current. Proc Natl Acad Sci U S A. Nov. 1986;83(21):8415-9.
Feany M.B., Bender WW. A Drosophila model of Parkinson's disease. Nature. Mar. 23, 2000;404(6776):394-8.
Feng, Y., Huynh, L., Takeyasu, K., and Fambrough, D. M. (1997). The Drosophila Na,K-ATPase alpha-subunit gene: gene structure, promoter function and analysis of a cold-sensitive recessive-lethal mutation, Genes Funct 1, 99-117.
Fletcher, C. F., C. M. Lutz, T. N. O'Sullivan, J. D. Shaughnessy, Jr., R. Hawkes et al., 1996 Absence epilepsy in tottering mutant mice is associated with calcium channel defects. Cell 87: 607-617.
Forman MS, Lee VM, Trojanowski JQ. New insights into genetic and molecular mechanisms of brain degeneration in tauopathies. J Chem Neuroanat. Dec. 2000;20(3-4):225-44. Review.
Fortini, M. E., and N. M. Bonini, 2000 Modeling human neurodegenerative diseases in Drosophila: on a wing and a prayer. Trends Genet 16: 161-167.

(Continued)

*Primary Examiner*—Scott D. Priebe
(74) *Attorney, Agent, or Firm*—Quarles & Brady LLP

(57) ABSTRACT

A method for obtaining a Drosophila neurodegeneration mutant includes the steps of selecting at least one Drosophila mutant having an aberrant phenotype selected from the group consisting of temperature-sensitive paralysis and bang-sensitive paralysis; and screening the at least one selected Drosophila mutant for age-dependent neurodegeneration. Neurodegeneration mutants are obtained in the method and causal mutations are characterized. The neurodegeneration mutants can be used in screening methods to identify putative neuroprotective agents.

4 Claims, No Drawings

OTHER PUBLICATIONS

Ganetzky B. Yuichiro Hiraizumi and forty years of segregation distortion. Genetics. May 1999;152(1):1-4. No abstract available.

Goedert, M., 2001 The significance of tau and alpha-synuclein inclusions in neurodegenerative diseases. Curr Opin Genet Dev 11: 343-351.

Hall, D. H., G. Gu, J. Garcia-Anoveros, L. Gong, M. Chalfie, et al., 1997 Neuropathology of degenerative cell death in *Caenorhabditis elegans*. J Neurosci 17; 1033-1045.

Heintz, N., and H. Y. Zoghbi, 2000 Insights from mouse models into the molecular basis of neurodegeneration. Annu Rev Physiol 62: 779-802.

Heisenberg M, Bohl K, 1979 Isolation of anatomical brain mutants of Drosophila by histological means. Z. Naturforsch. 34c: 143-147.

Kasbekar, D. P., Nelson, J. C., and Hall, L. M. (1987). Enhancer of seizure: a new genetic locus in *Drosophila melanogaster* defined by interactions with temperature-sensitive paralytic mutations, Genetics 116, 423-31.

Kretzschmar D, Hasan G, Sharma S, Heisenberg M, Benzer S. The swiss cheese mutant causes glial hyperwrapping and brain degeneration in Drosophila. J Neurosci. Oct. 1, 1997;17(19):7425-32.

Kuebler D, Tanouye MA. Modifications of seizure susceptibility in Drosophila. J Neurophysiol. Feb. 2000;83(2):998-1009.

Kuebler D, Zhang H, Ren X, Tanouye MA. Genetic suppression of seizure susceptibility in Drosophila. J Neurophysiol. Sep. 2001;86(3):1211-25.

Lebovitz RM, Takeyasu K, Fambrough DM. Molecular characterization and expression of the (Na+ + K+)-ATPase alpha-subunit in *Drosophila melanogaster*. Embo J. Jan. 1989;8(1):193-202.

Lees GJ, Leong W. Interactions between excitotoxins and the Na+/K+-ATPase inhibitor ouabain in causing neuronal lesions in the rat hippocampus. Brain Res. Apr. 1, 1996;714(1-2):145-55.

Lees GJ, Leong W. Brain lesions induced by specific and non-specific inhibitors of sodium-potassium ATPase. Brain Res. Jun. 27, 1994;649(1-2):225-33.

Lees, GJ. Contributory mechanisms in the causation of neurodegenerative disorders. Neuroscience. May 1993;54(2):287-322.

Littleton JT, Barnard RJ, Titus SA, Slind J, Chapman ER, Ganetzky B. SNARE-complex disassembly by NSF follows synaptic-vesicle fusion. Proc Natl Acad Sci U S A. Oct. 9, 2001;98(21):12233-8.

Littleton JT, Chapman ER, Kreber R, Garment MB, Carlson SD, Ganetzky B. Temperature-sensitive paralytic mutations demonstrate that synaptic exocytosis requires SNARE complex assembly and disassembly. Neuron. Aug. 1998;21(2):401-13.

Littleton, JT, L. Pallanck and B. Ganetzky, 1999 Mechanisms of neurotransmitter release, pp. 139-161 in Int Rev Neurobiol 43, edited by V. Budnik and L. S. Gramates. Academic Press, San Diego.

Loughney K, Kreber R, Ganetzky B. Molecular analysis of the para locus, a sodium channel gene in Drosophila. Cell. Sep. 22, 1989;58(6):1143-54.

Lutsenko, S., and Kaplan, J. H. (1994). Molecular events in close proximity to the membrane associated with the binding of ligands to the Na,K-ATPase, J Biol Chem 269, 4555-64.

Maccioni RB, Munoz JP, Barbeito L. The molecular bases of Alzheimer's disease and other neurodegenerative disorders. Arch Med Res. Sep.-Oct. 2001;32(5):367-81. Review.

Magyar JP, Bartsch U, Wang ZQ, Howells N, Aguzzi A, Wagner EF, Schachner M. Degeneration of neural cells in the central nervous system of mice deficient in the gene for the adhesion molecule on Glia, the beta 2 subunit of murine Na,K-ATPase. J Cell Biol. Nov. 1994;127(3):835-45.

Min KT, Benzer S. Spongecake and eggroll: two hereditary diseases in Drosophila resemble patterns of human brain degeneration. Curr Biol. Nov. 1, 1997;7(11):885-8.

Mobasheri, A., Avila, J., Cozar-Castellano, I., Brownleader, M. D., Trevan, M., Francis, M. J., Lamb, J. F., and Martin-Vasallo, P. (2000). Na+, K+-ATPase isozyme diversity; comparative biochemistry and physiological implications of novel functional interactions, Biosci Rep 20, 51-91.

Molthagen M, Schachner M, Bartsch U. Apoptotic cell death of photoreceptor cells in mice deficient for the adhesion molecule on glia (AMOG, the beta 2-subunit of the Na, K-ATPase). J Neurocytol. Apr. 1996;25(4):243-55.

Murtomaki S, Trenkner E, Wright JM, Saksela O, Liesi P. Increased proteolytic activity of the granule neurons may contribute to neuronal death in the weaver mouse cerebellum. Dev Biol. Apr. 1995;168(2):635-48.

Norman DJ, Feng L, Cheng SS, Gubbay J, Chan E, Heintz N. The lurcher gene induces apoptotic death in cerebellar Purkinje cells. Development. Apr. 1995;121(4):1183-93.

Ordway RW, Pallanck L, Ganetzky B. Neurally expressed Drosophila genes encoding homologs of the NSF and SNAP secretory proteins. Proc Natl Acad Sci U S A. Jun. 7, 1994;91(12):5715-9.

Palladino MJ, Keegan LP, O'Connell MA, Reenan RA. dADAR, a Drosophila double-stranded RNA-specific adenosine deaminase is highly developmentally regulated and is itself a target for RNA editing. RNA. Jul. 2000;6(7):1004-18.

Pallanck L, Ordway RW, Ganetzky B. A Drosophila NSF mutant. Nature. Jul. 6, 1995;376(6535):25.

Pallanck L, Ordway RW, Ramaswami M, Chi WY, Krishnan KS, Ganetzky B. Distinct roles for N-ethylmaleimide-sensitive fusion protein (NSF) suggested by J Biol Chem. Aug. 11, 1995;270(32):18742-4.

Pavlidis, P, and Tanouye, MA. Seizures and failures in the giant fiber pathway of Drosophila bang-sensitive paralytic mutants. J Neurosci. Aug. 1995;15(8):5810-9.

Renkawek, K., Renier, W. O., De Pont, J. J., Vogels, O. J., and Gabreels, F. J. (1992). Neonatal status convulsivus, spongiform encephalopathy, and low activity of Na+/K(+)-ATPase in the brain, Epilepsia 33, 58-64.

Schubiger M, Feng Y, Fambrough DM, Palka J. A mutation of the Drosophila sodium pump alpha subunit gene results in bang-sensitive paralysis. Neuron. Feb. 1994;12(2):373-81.

Sipione, S., and E. Cattaneo, 2001 Modeling huntington's disease in cells, flies, and mice. Mol Neurobiol 23: 21-51.

Sun, B., Wang, W., and Salvaterra, P. M. (1998). Functional analysis and tissue-specific expression of Drosophila Na+,K+-ATPase subunits, J Neurochem 71, 142-51.

Sun, B., Xu, P., Wang, W., and Salvaterra, P. M. (2001). In vivo modification of Na(+),K(+)-ATPase activity in Drosophila, Comp Biochem Physiol B Biochem Mol Biol 130, 521-36.

Taniguchi, K., Kaya, S., Abe, K., and Mardh, S. (2001). The oligomeric nature of Na/K-transport ATPase, J Biochem (Tokyo) 129, 335-42.

Therien, A. G., and Blostein, R. (2000). Mechanisms of sodium pump regulation, Am J Physiol Cell Physiol 279, C541-66.

Titus, S. A., Warmke, J. W., and Ganetzky, B. (1997). The Drosophila erg K+ channel polypeptide is encoded by the seizure locus, J Neurosci 17, 875-881.

Wang XJ, Reynolds ER, Deak P, Hall LM. The seizure locus encodes the Drosophila homolog of the HERG potassium channel. J Neurosci. Feb. 1, 1997;17(3):882-90.

Wu, C. F., and B. Ganetzky, 1992 Neurogenetic studies of ion channels in Drosophila, pp. 261-314 in Ion Channels 3, edited by T Narahashi. Plenum Press, New York.

Wu, C. F., Ganetzky, B., Jan, L. Y., and Jan, Y. N. (1978). A Drosophila mutant with a temperature-sensitive block in nerve conduction, Proc Natl Acad Sci U S A 75, 4047-51.

Zuo J, De Jager PL, Takahashi KA, Jiang W, Linden DJ, Heintz N. Neurodegeneration in Lurcher mice caused by mutation in delta2 glutamate receptor gene. Nature. Aug. 21, 1997;388(6644):769-73.

* cited by examiner

SEQUENCE LISTING

```
<160> NUMBER OF SEQ ID NOS: 20

<210> SEQ ID NO 1
<211> LENGTH: 1002
<212> TYPE: PRT
<213> ORGANISM: Drosophila melanogaster

<400> SEQUENCE: 1

Met Pro Ala Lys Val Asn Lys Lys Glu Asn Leu Asp Asp Leu Lys Gln
 1               5                  10                  15

Glu Leu Asp Ile Asp Phe His Lys Ile Ser Pro Glu Glu Leu Tyr Gln
            20                  25                  30

Arg Phe Gln Thr His Pro Glu Asn Gly Leu Ser His Ala Lys Ala Lys
```

-continued

```
                35                  40                  45
Glu Asn Leu Glu Arg Asp Gly Pro Asn Ala Leu Thr Pro Pro Lys Gln
 50                      55                  60

Thr Pro Glu Trp Val Lys Phe Cys Lys Asn Leu Phe Gly Gly Phe Ala
 65                  70                  75                  80

Met Leu Leu Trp Ile Gly Ala Ile Leu Cys Phe Val Ala Tyr Ser Ile
                 85                  90                  95

Gln Ala Ser Thr Ser Glu Glu Pro Ala Asp Asp Asn Leu Tyr Leu Gly
                100                 105                 110

Ile Val Leu Ser Ala Val Val Ile Val Thr Gly Ile Phe Ser Tyr Tyr
                115                 120                 125

Gln Glu Ser Lys Ser Ser Lys Ile Met Glu Ser Phe Lys Asn Met Val
            130                 135                 140

Pro Gln Phe Ala Thr Val Ile Arg Glu Gly Glu Lys Leu Thr Leu Arg
145                 150                 155                 160

Ala Glu Asp Leu Val Leu Gly Asp Val Val Glu Val Lys Phe Gly Asp
                165                 170                 175

Arg Ile Pro Ala Asp Ile Arg Ile Ile Glu Ala Arg Asn Phe Lys Val
            180                 185                 190

Asp Asn Ser Ser Leu Thr Gly Glu Ser Glu Pro Gln Ser Arg Gly Ala
            195                 200                 205

Glu Phe Thr His Glu Asn Pro Leu Glu Thr Lys Asn Leu Ala Phe Phe
            210                 215                 220

Ser Thr Asn Ala Val Glu Gly Thr Ala Lys Gly Val Val Ile Ser Cys
225                 230                 235                 240

Gly Asp His Thr Val Met Gly Arg Ile Ala Gly Leu Ala Ser Gly Leu
                245                 250                 255

Asp Thr Gly Glu Thr Pro Ile Ala Lys Glu Ile His His Phe Ile His
                260                 265                 270

Leu Ile Thr Gly Val Ala Val Phe Leu Gly Val Thr Phe Phe Val Ile
            275                 280                 285

Ala Phe Ile Leu Gly Tyr His Trp Leu Asp Ala Val Ile Phe Leu Ile
            290                 295                 300

Gly Ile Ile Val Ala Asn Val Pro Glu Gly Leu Leu Ala Thr Val Thr
305                 310                 315                 320

Val Cys Leu Thr Leu Thr Ala Lys Arg Met Ala Ser Lys Asn Cys Leu
                325                 330                 335

Val Lys Asn Leu Glu Ala Val Glu Thr Leu Gly Ser Thr Ser Thr Ile
            340                 345                 350

Cys Ser Asp Lys Thr Gly Thr Leu Thr Gln Asn Arg Met Thr Val Ala
            355                 360                 365

His Met Trp Phe Asp Asn Gln Ile Ile Glu Ala Asp Thr Thr Glu Asp
            370                 375                 380

Gln Ser Gly Val Gln Tyr Asp Arg Thr Ser Pro Gly Phe Lys Ala Leu
385                 390                 395                 400

Ser Arg Ile Ala Thr Leu Cys Asn Arg Ala Glu Phe Lys Gly Gly Gln
                405                 410                 415

Asp Gly Val Pro Ile Leu Lys Lys Glu Val Ser Gly Asp Ala Ser Glu
                420                 425                 430

Ala Ala Leu Leu Lys Cys Met Glu Leu Ala Leu Gly Asp Val Met Asn
            435                 440                 445

Ile Arg Lys Arg Asn Lys Lys Ile Ala Glu Val Pro Phe Asn Ser Thr
450                 455                 460
```

```
Asn Lys Tyr Gln Val Ser Ile His Glu Thr Glu Asp Thr Asn Asp Pro
465                 470                 475                 480

Arg Tyr Leu Leu Val Met Lys Gly Ala Pro Glu Arg Ile Leu Glu Arg
                485                 490                 495

Cys Ser Thr Ile Phe Ile Asn Gly Lys Glu Lys Val Leu Asp Glu Glu
            500                 505                 510

Met Lys Glu Ala Phe Asn Asn Ala Tyr Met Glu Leu Gly Gly Leu Gly
        515                 520                 525

Glu Arg Val Leu Gly Phe Cys Asp Phe Met Leu Pro Ser Asp Lys Tyr
    530                 535                 540

Pro Asn Gly Phe Lys Phe Asn Thr Asp Asp Ile Asn Phe Pro Ile Asp
545                 550                 555                 560

Asn Leu Arg Phe Val Gly Leu Met Ser Met Ile Asp Pro Pro Arg Ala
                565                 570                 575

Ala Val Pro Asp Ala Val Ala Lys Cys Arg Ser Ala Gly Ile Lys Val
            580                 585                 590

Ile Met Val Thr Gly Asp His Pro Ile Thr Ala Lys Ala Ile Ala Lys
        595                 600                 605

Ser Val Gly Ile Ile Ser Glu Gly Asn Glu Thr Val Glu Asp Ile Ala
    610                 615                 620

Gln Arg Leu Asn Ile Pro Val Ser Glu Val Asn Pro Arg Glu Ala Lys
625                 630                 635                 640

Ala Ala Val Val His Gly Ala Glu Leu Arg Asp Val Ser Ser Asp Gln
                645                 650                 655

Leu Asp Glu Ile Leu Arg Tyr His Thr Glu Ile Val Phe Ala Arg Thr
            660                 665                 670

Ser Pro Gln Gln Lys Leu Ile Ile Val Glu Gly Cys Gln Arg Met Gly
        675                 680                 685

Ala Ile Val Ala Val Thr Gly Asp Gly Val Asn Asp Ser Pro Ala Leu
    690                 695                 700

Lys Lys Ala Asp Ile Gly Val Ala Met Gly Ile Ala Gly Ser Asp Val
705                 710                 715                 720

Ser Lys Gln Ala Ala Asp Met Ile Leu Leu Asp Asp Asn Phe Ala Ser
                725                 730                 735

Ile Val Thr Gly Val Glu Glu Gly Arg Leu Ile Phe Asp Asn Leu Lys
            740                 745                 750

Lys Ser Ile Ala Tyr Thr Leu Thr Ser Asn Ile Pro Glu Ile Ser Pro
        755                 760                 765

Phe Leu Ala Phe Ile Leu Cys Asp Ile Pro Leu Pro Leu Gly Thr Val
    770                 775                 780

Thr Ile Leu Cys Ile Asp Leu Gly Thr Asp Met Val Pro Ala Ile Ser
785                 790                 795                 800

Leu Ala Tyr Glu His Ala Glu Ala Asp Ile Met Lys Arg Pro Pro Arg
                805                 810                 815

Asp Pro Phe Asn Asp Lys Leu Val Asn Ser Arg Leu Ile Ser Met Ala
            820                 825                 830

Tyr Gly Gln Ile Gly Met Ile Gln Ala Ala Gly Phe Phe Val Tyr
        835                 840                 845

Phe Val Ile Met Ala Glu Asn Gly Phe Leu Pro Lys Lys Leu Phe Gly
    850                 855                 860

Ile Arg Lys Met Trp Asp Ser Lys Ala Val Asn Asp Leu Thr Asp Ser
865                 870                 875                 880
```

-continued

```
Tyr Gly Gln Glu Trp Thr Tyr Arg Asp Arg Lys Thr Leu Glu Tyr Thr
            885                 890                 895

Cys His Thr Ala Phe Phe Ile Ser Ile Val Val Gln Trp Ala Asp
        900                 905                 910

Leu Ile Ile Cys Lys Thr Arg Arg Asn Ser Ile Phe Gln Gln Gly Met
            915                 920                 925

Arg Asn Trp Ala Leu Asn Phe Gly Leu Val Phe Glu Thr Val Leu Ala
930                 935                 940

Ala Phe Leu Ser Tyr Cys Pro Gly Met Glu Lys Gly Leu Arg Met Tyr
945                 950                 955                 960

Pro Leu Lys Leu Val Trp Trp Phe Pro Ala Ile Pro Phe Ala Leu Ala
            965                 970                 975

Ile Phe Ile Tyr Asp Glu Thr Arg Arg Phe Tyr Leu Arg Arg Asn Pro
            980                 985                 990

Gly Gly Trp Leu Glu Gln Glu Thr Tyr Tyr
            995                 1000
```

<210> SEQ ID NO 2
<211> LENGTH: 95
<212> TYPE: DNA
<213> ORGANISM: Drosophila melanogaster
<220> FEATURE:
<221> NAME/KEY: CDS
<222> LOCATION: (1)..(93)

<400> SEQUENCE: 2

```
att cct gcc ata tca ctg gcc tac gag gga ccc gag gct gac atc atg     48
Ile Pro Ala Ile Ser Leu Ala Tyr Glu Gly Pro Glu Ala Asp Ile Met
1               5                   10                  15 aag cgc cgg ccg cgc aat ccg gag atc gat aac cta gtc aac gag ag     95
Lys Arg Arg Pro Arg Asn Pro Glu Ile Asp Asn Leu Val Asn Glu
            20                  25                  30
```

<210> SEQ ID NO 3
<211> LENGTH: 31
<212> TYPE: PRT
<213> ORGANISM: Drosophila melanogaster

<400> SEQUENCE: 3

```
Ile Pro Ala Ile Ser Leu Ala Tyr Glu Gly Pro Glu Ala Asp Ile Met
1               5                   10                  15

Lys Arg Arg Pro Arg Asn Pro Glu Ile Asp Asn Leu Val Asn Glu
            20                  25                  30
```

<210> SEQ ID NO 4
<211> LENGTH: 95
<212> TYPE: DNA
<213> ORGANISM: Drosophila melanogaster
<220> FEATURE:
<221> NAME/KEY: CDS
<222> LOCATION: (1)..(93)

<400> SEQUENCE: 4

```
gtg cca gcc att tca ttg gcc tac gag cat gcc gaa gcc gat att atg     48
Val Pro Ala Ile Ser Leu Ala Tyr Glu His Ala Glu Ala Asp Ile Met
1               5                   10                  15 aag cgt cca cca cgt gac ccc ttc aac gat aaa tta gtg aac tca ag     95
Lys Arg Pro Pro Arg Asp Pro Phe Asn Asp Lys Leu Val Asn Ser
            20                  25                  30
```

<210> SEQ ID NO 5
<211> LENGTH: 31

```
<212> TYPE: PRT
<213> ORGANISM: Drosophila melanogaster

<400> SEQUENCE: 5

Val Pro Ala Ile Ser Leu Ala Tyr Glu His Ala Glu Ala Asp Ile Met
 1               5                  10                  15

Lys Arg Pro Pro Arg Asp Pro Phe Asn Asp Lys Leu Val Asn Ser
                20                  25                  30

<210> SEQ ID NO 6
<211> LENGTH: 95
<212> TYPE: DNA
<213> ORGANISM: Drosophila melanogaster
<220> FEATURE:
<221> NAME/KEY: CDS
<222> LOCATION: (1)..(93)

<400> SEQUENCE: 6 gtg cca gcc att tcc tta gct tat gag acg gct gaa tcc gat att atg      48
Val Pro Ala Ile Ser Leu Ala Tyr Glu Thr Ala Glu Ser Asp Ile Met
 1               5                  10                  15 aaa cgc cag ccg agg aac ccc ttc caa gat aaa ctg gtc aac gaa ag       95
Lys Arg Gln Pro Arg Asn Pro Phe Gln Asp Lys Leu Val Asn Glu
                20                  25                  30

<210> SEQ ID NO 7
<211> LENGTH: 31
<212> TYPE: PRT
<213> ORGANISM: Drosophila melanogaster

<400> SEQUENCE: 7

Val Pro Ala Ile Ser Leu Ala Tyr Glu Thr Ala Glu Ser Asp Ile Met
 1               5                  10                  15

Lys Arg Gln Pro Arg Asn Pro Phe Gln Asp Lys Leu Val Asn Glu
                20                  25                  30

<210> SEQ ID NO 8
<211> LENGTH: 95
<212> TYPE: DNA
<213> ORGANISM: Drosophila melanogaster
<220> FEATURE:
<221> NAME/KEY: CDS
<222> LOCATION: (1)..(93)

<400> SEQUENCE: 8 att ccg gcc att tca ctc gct tac gag caa gcc gag agc gat att atg      48
Ile Pro Ala Ile Ser Leu Ala Tyr Glu Gln Ala Glu Ser Asp Ile Met
 1               5                  10                  15 aag cgt cag ccg aga gat ccg tat cgc gac aac ttg gtg aac cgc ag       95
Lys Arg Gln Pro Arg Asp Pro Tyr Arg Asp Asn Leu Val Asn Arg
                20                  25                  30

<210> SEQ ID NO 9
<211> LENGTH: 31
<212> TYPE: PRT
<213> ORGANISM: Drosophila melanogaster

<400> SEQUENCE: 9

Ile Pro Ala Ile Ser Leu Ala Tyr Glu Gln Ala Glu Ser Asp Ile Met
 1               5                  10                  15

Lys Arg Gln Pro Arg Asp Pro Tyr Arg Asp Asn Leu Val Asn Arg
                20                  25                  30

<210> SEQ ID NO 10
```

```
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
ttaatagtag gtctcctgct cc                                              22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
tcaacaccga cgacatcaac ttc                                             23

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
ggttgcggcg caagtagaaa cgacg                                           25

<210> SEQ ID NO 13
<211> LENGTH: 10
<212> TYPE: PRT
<213> ORGANISM: Drosophila melanogaster

<400> SEQUENCE: 13

Tyr Thr Leu Thr Ser Asn Ile Pro Glu Ile
 1               5                  10

<210> SEQ ID NO 14
<211> LENGTH: 1041
<212> TYPE: PRT
<213> ORGANISM: Drosophila melanogaster

<400> SEQUENCE: 14

Met Ala Leu Arg Ser Asp Tyr Glu His Gly Arg Ala Asp Ser Tyr Arg
 1               5                  10                  15

Val Ala Thr Val Ile Ala Thr Asp Asp Asn Arg Thr Ala Asp Gly
             20                  25                  30

Gln Tyr Lys Ser Arg Arg Lys Met Pro Ala Lys Val Asn Lys Lys Glu
         35                  40                  45

Asn Leu Asp Asp Leu Lys Gln Glu Leu Asp Ile Asp Phe His Lys Ile
     50                  55                  60

Ser Pro Glu Glu Leu Tyr Gln Arg Phe Gln Thr His Pro Glu Asn Gly
 65                  70                  75                  80

Leu Ser His Ala Lys Ala Lys Glu Asn Leu Glu Arg Asp Gly Pro Asn
                 85                  90                  95

Ala Leu Thr Pro Pro Lys Gln Thr Pro Glu Trp Val Lys Phe Cys Lys
            100                 105                 110

Asn Leu Phe Gly Gly Phe Ala Met Leu Leu Trp Ile Gly Ala Ile Leu
        115                 120                 125

Cys Phe Val Ala Tyr Ser Ile Gln Ala Ser Thr Ser Glu Glu Pro Ala
    130                 135                 140
```

```
Asp Asp Asn Leu Tyr Leu Gly Ile Val Leu Ser Ala Val Val Ile Val
145                 150                 155                 160

Thr Gly Ile Phe Ser Tyr Tyr Gln Glu Ser Lys Ser Ser Lys Ile Met
            165                 170                 175

Glu Ser Phe Lys Asn Met Val Pro Gln Phe Ala Thr Val Ile Arg Glu
            180                 185                 190

Gly Glu Lys Leu Thr Leu Arg Ala Glu Asp Leu Val Leu Gly Asp Val
            195                 200                 205

Val Glu Val Lys Phe Gly Asp Arg Ile Pro Ala Asp Ile Arg Ile Ile
210                 215                 220

Glu Ala Arg Asn Phe Lys Val Asp Asn Ser Ser Leu Thr Gly Glu Ser
225                 230                 235                 240

Glu Pro Gln Ser Arg Gly Ala Glu Phe Thr His Glu Asn Pro Leu Glu
            245                 250                 255

Thr Lys Asn Leu Ala Phe Phe Ser Thr Asn Ala Val Glu Gly Thr Ala
            260                 265                 270

Lys Gly Val Val Ile Ser Cys Gly Asp His Thr Val Met Gly Arg Ile
            275                 280                 285

Ala Gly Leu Ala Ser Gly Leu Asp Thr Gly Glu Thr Pro Ile Ala Lys
            290                 295                 300

Glu Ile His His Phe Ile His Leu Ile Thr Gly Val Ala Val Phe Leu
305                 310                 315                 320

Gly Val Thr Phe Phe Val Ile Ala Phe Ile Leu Gly Tyr His Trp Leu
            325                 330                 335

Asp Ala Val Ile Phe Leu Ile Gly Ile Ile Val Ala Asn Val Pro Glu
            340                 345                 350

Gly Leu Leu Ala Thr Val Thr Val Cys Leu Thr Leu Thr Ala Lys Arg
            355                 360                 365

Met Ala Ser Lys Asn Cys Leu Val Lys Asn Leu Glu Ala Val Glu Thr
            370                 375                 380

Leu Gly Ser Thr Ser Thr Ile Cys Ser Asp Lys Thr Gly Thr Leu Thr
385                 390                 395                 400

Gln Asn Arg Met Thr Val Ala His Met Trp Phe Asp Asn Gln Ile Ile
            405                 410                 415

Glu Ala Asp Thr Thr Glu Asp Gln Ser Gly Val Gln Tyr Asp Arg Thr
            420                 425                 430

Ser Pro Gly Phe Lys Ala Leu Ser Arg Ile Ala Thr Leu Cys Asn Arg
            435                 440                 445

Ala Glu Phe Lys Gly Gly Gln Asp Gly Val Pro Ile Leu Lys Lys Glu
            450                 455                 460

Val Ser Gly Asp Ala Ser Glu Ala Ala Leu Leu Lys Cys Met Glu Leu
465                 470                 475                 480

Ala Leu Gly Asp Val Met Asn Ile Arg Lys Arg Asn Lys Lys Ile Ala
            485                 490                 495

Glu Val Pro Phe Asn Ser Thr Asn Lys Tyr Gln Val Ser Ile His Glu
            500                 505                 510

Thr Glu Asp Thr Asn Asp Pro Arg Tyr Leu Leu Val Met Lys Gly Ala
            515                 520                 525

Pro Glu Arg Ile Leu Glu Arg Cys Ser Thr Ile Phe Ile Asn Gly Lys
            530                 535                 540

Glu Lys Val Leu Asp Glu Glu Met Lys Glu Ala Phe Asn Asn Ala Tyr
545                 550                 555                 560
```

```
Met Glu Leu Gly Gly Leu Gly Glu Arg Val Leu Gly Phe Cys Asp Phe
                565                 570                 575

Met Leu Pro Ser Asp Lys Tyr Pro Asn Gly Phe Lys Phe Asn Thr Asp
                580                 585                 590

Asp Ile Asn Phe Pro Ile Asp Asn Leu Arg Phe Val Gly Leu Met Ser
                595                 600                 605

Met Ile Asp Pro Pro Arg Ala Ala Val Pro Asp Ala Val Ala Lys Cys
        610                 615                 620

Arg Ser Ala Gly Ile Lys Val Ile Met Val Thr Gly Asp His Pro Ile
625                 630                 635                 640

Thr Ala Lys Ala Ile Ala Lys Ser Val Gly Ile Ile Ser Glu Gly Asn
                    645                 650                 655

Glu Thr Val Glu Asp Ile Ala Gln Arg Leu Asn Ile Pro Val Ser Glu
                660                 665                 670

Val Asn Pro Arg Glu Ala Lys Ala Ala Val Val His Gly Ala Glu Leu
            675                 680                 685

Arg Asp Val Ser Ser Asp Gln Leu Asp Glu Ile Leu Arg Tyr His Thr
690                 695                 700

Glu Ile Val Phe Ala Arg Thr Ser Pro Gln Gln Lys Leu Ile Ile Val
705                 710                 715                 720

Glu Gly Cys Gln Arg Met Gly Ala Ile Val Ala Val Thr Gly Asp Gly
                    725                 730                 735

Val Asn Asp Ser Pro Ala Leu Lys Lys Ala Asp Ile Gly Val Ala Met
                740                 745                 750

Gly Ile Ala Gly Ser Asp Val Ser Lys Gln Ala Ala Asp Met Ile Leu
            755                 760                 765

Leu Asp Asp Asn Phe Ala Ser Ile Val Thr Gly Val Glu Glu Gly Arg
770                 775                 780

Leu Ile Phe Asp Asn Leu Lys Lys Ser Ile Ala Tyr Thr Leu Thr Ser
785                 790                 795                 800

Asn Ile Pro Glu Ile Ser Pro Phe Leu Ala Phe Ile Leu Cys Asp Ile
                    805                 810                 815

Pro Leu Pro Leu Gly Thr Val Thr Ile Leu Cys Ile Asp Leu Gly Thr
                820                 825                 830

Asp Met Val Pro Ala Ile Ser Leu Ala Tyr Glu His Ala Glu Ala Asp
            835                 840                 845

Ile Met Lys Arg Pro Pro Arg Asp Pro Phe Asn Asp Lys Leu Val Asn
850                 855                 860

Ser Arg Leu Ile Ser Met Ala Tyr Gly Gln Ile Gly Met Ile Gln Ala
865                 870                 875                 880

Ala Ala Gly Phe Phe Val Tyr Phe Val Ile Met Ala Glu Asn Gly Phe
                    885                 890                 895

Leu Pro Lys Lys Leu Phe Gly Ile Arg Lys Met Trp Asp Ser Lys Ala
                900                 905                 910

Val Asn Asp Leu Thr Asp Ser Tyr Gly Gln Glu Trp Thr Tyr Arg Asp
            915                 920                 925

Arg Lys Thr Leu Glu Tyr Thr Cys His Thr Ala Phe Phe Ile Ser Ile
930                 935                 940

Val Val Val Gln Trp Ala Asp Leu Ile Ile Cys Lys Thr Arg Arg Asn
945                 950                 955                 960

Ser Ile Phe Gln Gln Gly Met Arg Asn Trp Ala Leu Asn Phe Gly Leu
                    965                 970                 975

Val Phe Glu Thr Val Leu Ala Ala Phe Leu Ser Tyr Cys Pro Gly Met
```

```
                980             985             990
Glu Lys Gly Leu Arg Met Tyr Pro Leu Lys Leu Val Trp Trp Phe Pro
        995                1000                1005

Ala Ile Pro Phe Ala Leu Ala Ile Phe Ile Tyr Asp Glu Thr Arg Arg
    1010                1015                1020

Phe Tyr Leu Arg Arg Asn Pro Gly Gly Trp Leu Glu Gln Glu Thr Tyr
1025                1030                1035                1040

Tyr

<210> SEQ ID NO 15
<211> LENGTH: 1037
<212> TYPE: PRT
<213> ORGANISM: Drosophila melanogaster

<400> SEQUENCE: 15

Met Ser Ala Gln His Gly Arg Ala Asp Ser Tyr Arg Val Ala Thr Val
  1               5                  10                  15

Ile Ala Thr Asp Asp Asn Arg Thr Ala Asp Gly Gln Tyr Lys Ser
                 20                  25                  30

Arg Arg Lys Met Pro Ala Lys Val Asn Lys Glu Asn Leu Asp Asp
         35                  40                  45

Leu Lys Gln Glu Leu Asp Ile Asp Phe His Lys Ile Ser Pro Glu Glu
     50                  55                  60

Leu Tyr Gln Arg Phe Gln Thr His Pro Glu Asn Gly Leu Ser His Ala
 65                  70                  75                  80

Lys Ala Lys Glu Asn Leu Glu Arg Asp Gly Pro Asn Ala Leu Thr Pro
                 85                  90                  95

Pro Lys Gln Thr Pro Glu Trp Val Lys Phe Cys Lys Asn Leu Phe Gly
                100                 105                 110

Gly Phe Ala Met Leu Leu Trp Ile Gly Ala Ile Leu Cys Phe Val Ala
            115                 120                 125

Tyr Ser Ile Gln Ala Ser Thr Ser Glu Glu Pro Ala Asp Asp Asn Leu
    130                 135                 140

Tyr Leu Gly Ile Val Leu Ser Ala Val Val Ile Val Thr Gly Ile Phe
145                 150                 155                 160

Ser Tyr Tyr Gln Glu Ser Lys Ser Ser Lys Ile Met Glu Ser Phe Lys
                165                 170                 175

Asn Met Val Pro Gln Phe Ala Thr Val Ile Arg Glu Gly Glu Lys Leu
            180                 185                 190

Thr Leu Arg Ala Glu Asp Leu Val Leu Gly Asp Val Val Glu Val Lys
    195                 200                 205

Phe Gly Asp Arg Ile Pro Ala Asp Ile Arg Ile Ile Glu Ala Arg Asn
    210                 215                 220

Phe Lys Val Asp Asn Ser Ser Leu Thr Gly Glu Ser Glu Pro Gln Ser
225                 230                 235                 240

Arg Gly Ala Glu Phe Thr His Glu Asn Pro Leu Glu Thr Lys Asn Leu
                245                 250                 255

Ala Phe Phe Ser Thr Asn Ala Val Glu Gly Thr Ala Lys Gly Val Val
            260                 265                 270

Ile Ser Cys Gly Asp His Thr Val Met Gly Arg Ile Ala Gly Leu Ala
    275                 280                 285

Ser Gly Leu Asp Thr Gly Glu Thr Pro Ile Ala Lys Glu Ile His His
    290                 295                 300

Phe Ile His Leu Ile Thr Gly Val Ala Val Phe Leu Gly Val Thr Phe
```

-continued

```
            305                 310                 315                 320
Phe Val Ile Ala Phe Ile Leu Gly Tyr His Trp Leu Asp Ala Val Ile
                325                 330                 335
Phe Leu Ile Gly Ile Ile Val Ala Asn Val Pro Glu Gly Leu Leu Ala
                340                 345                 350
Thr Val Thr Val Cys Leu Thr Leu Thr Ala Lys Arg Met Ala Ser Lys
                355                 360                 365
Asn Cys Leu Val Lys Asn Leu Glu Ala Val Glu Thr Leu Gly Ser Thr
        370                 375                 380
Ser Thr Ile Cys Ser Asp Lys Thr Gly Thr Leu Thr Gln Asn Arg Met
385                 390                 395                 400
Thr Val Ala His Met Trp Phe Asp Asn Gln Ile Ile Glu Ala Asp Thr
                405                 410                 415
Thr Glu Asp Gln Ser Gly Val Gln Tyr Asp Arg Thr Ser Pro Gly Phe
                420                 425                 430
Lys Ala Leu Ser Arg Ile Ala Thr Leu Cys Asn Arg Ala Glu Phe Lys
                435                 440                 445
Gly Gly Gln Asp Gly Val Pro Ile Leu Lys Lys Glu Val Ser Gly Asp
        450                 455                 460
Ala Ser Glu Ala Ala Leu Leu Lys Cys Met Glu Leu Ala Leu Gly Asp
465                 470                 475                 480
Val Met Asn Ile Arg Lys Arg Asn Lys Lys Ile Ala Glu Val Pro Phe
                485                 490                 495
Asn Ser Thr Asn Lys Tyr Gln Val Ser Ile His Glu Thr Glu Asp Thr
                500                 505                 510
Asn Asp Pro Arg Tyr Leu Leu Val Met Lys Gly Ala Pro Glu Arg Ile
        515                 520                 525
Leu Glu Arg Cys Ser Thr Ile Phe Ile Asn Gly Lys Glu Lys Val Leu
        530                 535                 540
Asp Glu Glu Met Lys Glu Ala Phe Asn Asn Ala Tyr Met Glu Leu Gly
545                 550                 555                 560
Gly Leu Gly Glu Arg Val Leu Gly Phe Cys Asp Phe Met Leu Pro Ser
                565                 570                 575
Asp Lys Tyr Pro Asn Gly Phe Lys Phe Asn Thr Asp Asp Ile Asn Phe
                580                 585                 590
Pro Ile Asp Asn Leu Arg Phe Val Gly Leu Met Ser Met Ile Asp Pro
        595                 600                 605
Pro Arg Ala Ala Val Pro Asp Ala Val Ala Lys Cys Arg Ser Ala Gly
        610                 615                 620
Ile Lys Val Ile Met Val Thr Gly Asp His Pro Ile Thr Ala Lys Ala
625                 630                 635                 640
Ile Ala Lys Ser Val Gly Ile Ile Ser Glu Gly Asn Glu Thr Val Glu
                645                 650                 655
Asp Ile Ala Gln Arg Leu Asn Ile Pro Val Ser Glu Val Asn Pro Arg
                660                 665                 670
Glu Ala Lys Ala Ala Val Val His Gly Ala Glu Leu Arg Asp Val Ser
                675                 680                 685
Ser Asp Gln Leu Asp Glu Ile Leu Arg Tyr His Thr Glu Ile Val Phe
        690                 695                 700
Ala Arg Thr Ser Pro Gln Gln Lys Leu Ile Ile Val Glu Gly Cys Gln
705                 710                 715                 720
Arg Met Gly Ala Ile Val Ala Val Thr Gly Asp Gly Val Asn Asp Ser
                725                 730                 735
```

-continued

```
Pro Ala Leu Lys Lys Ala Asp Ile Gly Val Ala Met Gly Ile Ala Gly
            740                 745                 750

Ser Asp Val Ser Lys Gln Ala Ala Asp Met Ile Leu Leu Asp Asp Asn
            755                 760                 765

Phe Ala Ser Ile Val Thr Gly Val Glu Glu Gly Arg Leu Ile Phe Asp
            770                 775                 780

Asn Leu Lys Lys Ser Ile Ala Tyr Thr Leu Thr Ser Asn Ile Pro Glu
785                 790                 795                 800

Ile Ser Pro Phe Leu Ala Phe Ile Leu Cys Asp Ile Pro Leu Pro Leu
                    805                 810                 815

Gly Thr Val Thr Ile Leu Cys Ile Asp Leu Gly Thr Asp Met Val Pro
                820                 825                 830

Ala Ile Ser Leu Ala Tyr Glu His Ala Glu Ala Asp Ile Met Lys Arg
            835                 840                 845

Pro Pro Arg Asp Pro Phe Asn Asp Lys Leu Val Asn Ser Arg Leu Ile
            850                 855                 860

Ser Met Ala Tyr Gly Gln Ile Gly Met Ile Gln Ala Ala Gly Phe
865                 870                 875                 880

Phe Val Tyr Phe Val Ile Met Ala Glu Asn Gly Phe Leu Pro Lys Lys
                    885                 890                 895

Leu Phe Gly Ile Arg Lys Met Trp Asp Ser Lys Ala Val Asn Asp Leu
                900                 905                 910

Thr Asp Ser Tyr Gly Gln Glu Trp Thr Tyr Arg Asp Arg Lys Thr Leu
            915                 920                 925

Glu Tyr Thr Cys His Thr Ala Phe Phe Ile Ser Ile Val Val Gln
    930                 935                 940

Trp Ala Asp Leu Ile Ile Cys Lys Thr Arg Arg Asn Ser Ile Phe Gln
945                 950                 955                 960

Gln Gly Met Arg Asn Trp Ala Leu Asn Phe Gly Leu Val Phe Glu Thr
                    965                 970                 975

Val Leu Ala Ala Phe Leu Ser Tyr Cys Pro Gly Met Glu Lys Gly Leu
                980                 985                 990

Arg Met Tyr Pro Leu Lys Leu Val Trp Trp Phe Pro Ala Ile Pro Phe
            995                 1000                1005

Ala Leu Ala Ile Phe Ile Tyr Asp Glu Thr Arg Arg Phe Tyr Leu Arg
    1010                1015                1020

Arg Asn Pro Gly Gly Trp Leu Glu Gln Glu Thr Tyr Tyr
1025                1030                1035

<210> SEQ ID NO 16
<211> LENGTH: 1041
<212> TYPE: PRT
<213> ORGANISM: Drosophila melanogaster

<400> SEQUENCE: 16

Met Met Gln Pro Pro Arg Lys Gly Asn Tyr Val Lys Phe Leu Lys
1               5                   10                  15

Asn Leu His Thr Glu Gln Val Ala Lys Leu Gln Leu Lys Asn Gln His
            20                  25                  30

Glu Cys Asp Leu Leu Glu Asp Ile Arg Gln Phe Thr Ile Lys Arg Ser
        35                  40                  45

Ala Val Glu Lys Ser Tyr Ser Glu Ser Leu Leu Lys Ile Ser Ser Gln
    50                  55                  60

Tyr Leu Asn Lys Lys Ile Pro Asn Ile Pro Asp Ile Lys Met Glu Gly
```

-continued

```
                65                  70                  75                  80
        Met Glu Glu Arg Trp Asn Met Trp Ser Val Trp Arg Thr Val Leu Glu
                            85                  90                  95

Glu Asn Glu Lys Leu Ala Arg Ala Arg Leu Ala Ala Ile Glu Val Phe
                        100                 105                 110

Gln Gln Gln Ile Ala Asp Glu Ala Lys Val Leu Arg Asp Tyr Lys Leu
                        115                 120                 125

Ala Ile Ala Lys Arg Ser Leu Ala Gly Ile Val Asn Val Gln Lys Glu
                    130                 135                 140

Leu His Leu Ser Val Gly Asp Val Asp Lys Thr Lys Lys Ser Tyr Phe
        145                 150                 155                 160

Asp Glu Glu His Cys Ala His Asp Val Arg Asp Lys Ala Arg Asp Ile
                            165                 170                 175

Glu Glu Lys Leu Lys Lys Lys Gly Ser Phe Phe Gln Ser Ile Thr
                        180                 185                 190

Ser Leu Gln Lys Asn Ser Ala Arg Val Thr Ser Arg Lys Glu Leu Leu
                        195                 200                 205

Glu Glu Lys Ser Ser Gly Ala Arg Asn Asp Tyr Val Leu Ser Leu Ala
                    210                 215                 220

Ala Ala Asn Ala His Gln Asn Arg Tyr Phe Thr Val Asp Leu Gln Thr
        225                 230                 235                 240

Thr Met Thr Thr Met Glu Asn Tyr Val Phe Glu Arg Val Ala Glu Tyr
                            245                 250                 255

Leu Met Leu Met Gly Arg Thr Glu Leu Leu Thr Cys Ser Ala Thr Gln
                        260                 265                 270

Asn Ser Phe Gly Lys Ile Arg Asp Gln Ala Gln Gln Leu Thr Arg Glu
                        275                 280                 285

Tyr Asn Leu Gln Cys Cys Tyr Leu Phe Tyr Pro Val Leu Lys Gln His
                    290                 295                 300

Ile Gln Tyr Asp Phe Glu Ala Cys Asp Asn Asp Pro Val Arg Lys Val
        305                 310                 315                 320

Thr Ala Glu His Glu Ser Ala Ala Glu Thr Leu Thr Lys Glu Ala Lys
                            325                 330                 335

Asn Leu Ala Gly Arg Val Val Lys Glu Asn Ala Ser Ile Arg Glu Asn
                        340                 345                 350

Ala Lys Lys Leu Ala Leu Cys Gln Ser Leu Arg Asp Ser Gly Gln Arg
                        355                 360                 365

Thr Asp Pro Asn Asp Pro Asn Gly Pro Asp Leu Asp Thr Lys Ile Glu
                    370                 375                 380

Glu Phe Arg Asp Gln Ile Arg Arg Ser Glu Thr Glu Lys Thr Lys Ala
        385                 390                 395                 400

Glu Ala Cys Leu Gln Cys Leu Arg Asp Gly Ile Asn Val Asp Glu
                            405                 410                 415

Trp Val Gln Glu Ala Glu Asn Met Gly Val Gln Glu Leu Thr Arg Ser
                        420                 425                 430

Ala Ser Ser Ile Ser Met Arg Thr Asp Ala Ser Gly Gln Gly Glu Asn
                        435                 440                 445

Pro Ser Ser Asp Ser Phe Tyr Asp Ser Asp Lys Glu Glu Thr Gln Ala
                    450                 455                 460

Ala Ala Gln Thr Lys Pro Lys Gln Glu Gln Gln Leu Ser Arg Asp Arg
        465                 470                 475                 480

Thr Phe Ser Asp Ser Glu Asp Glu Pro Glu Val Arg Pro Ser Ala Ala
                            485                 490                 495
```

-continued

```
Ala Ala Ser Ser Ala Ala Ala Ser Ser Ser Met Met Ala Ser Ser
            500                 505                 510
Ala Gly Gly Trp Asp Asp Pro Thr Glu Val Asn Trp Gly Ala Gly Glu
        515                 520                 525
Glu Glu Asp Asp Lys Asp Glu Pro Ile Val Pro Glu Pro Lys Glu Ala
        530                 535                 540
Ile Phe Lys Cys Thr Ala Leu Tyr Ser Tyr Thr Ala Gln Asn Pro Asp
545                 550                 555                 560
Glu Leu Thr Ile Val Glu Asn Glu Gln Leu Glu Val Val Gly Glu Gly
                565                 570                 575
Asp Gly Asp Gly Trp Leu Arg Ala Arg Asn Tyr Arg Gly Glu Glu Gly
            580                 585                 590
Tyr Val Pro His Asn Tyr Leu Asp Ile Asp Gln Glu Thr Ala Gly Ser
        595                 600                 605
Ala Phe Asn Gly Thr Ser Gly Asn Gln Leu Arg Ser Gln Ile Ser Phe
    610                 615                 620
Ser Ser Val Asp Tyr Thr Val Asp Asn Glu Asp Gln Thr Val Asp Ser
625                 630                 635                 640
Met Gln Ser Pro Asp Gln Val Ser Val Ile Met Ala Pro Gln Lys Arg
                645                 650                 655
Val Lys Ser Asp Val Glu Trp Cys Ile Ala Leu Tyr Asp Tyr Asp Ala
            660                 665                 670
Thr Ala Glu Asp Glu Leu Thr Phe Glu Glu Gly Asp Lys Ile Lys Ile
        675                 680                 685
Ile Thr Lys Thr Ala His Gly Val Asp Asp Gly Trp Trp Glu Gly Glu
    690                 695                 700
Leu Asp Gly Lys Phe Gly Asn Phe Pro Ser Leu Val Val Glu Glu Cys
705                 710                 715                 720
Asp Glu Met Gly Glu Pro Leu Ser Glu Gly Gly Asp Glu Ser Pro Pro
                725                 730                 735
Pro Thr Ala Ala Pro Thr Phe Ala Leu Pro Pro Ala Pro Ala Leu Pro
            740                 745                 750
Pro Glu Tyr Ala His Glu Leu Glu Leu Glu Leu Thr Glu Asp Met Phe
        755                 760                 765
Gly Ser Gln Asp Thr Ala Asp Glu Asp Ser Gly Tyr Ile Pro Asn Gly
    770                 775                 780
Ala Ala Ala Pro Ser Ile Pro Pro Gly Gln Asn Gln Ser Gln Thr
785                 790                 795                 800
Thr Ala Lys Lys Val Leu Ile Gln Glu Pro Gly Met Glu Asp Asp Leu
                805                 810                 815
Ser Asp Asp Gly Gln Pro Pro Pro Ser Leu Pro Pro Gln Leu Ala
            820                 825                 830
Lys Ala Gly Gly Ser Ala Pro Gly Ser Gly Ser Lys Val Glu Lys Gly
        835                 840                 845
Ala Ala Ala Gly Gly Ala Asn Thr Leu Asn Leu Gly Glu Ser Asp Ala
    850                 855                 860
Gln Pro Val Glu Pro Val Ser Glu Glu Gln Pro Ala Glu Val Ala Lys
865                 870                 875                 880
Lys Pro Asp Ile Ala Pro Lys Pro Leu Ala Lys Val Ala Pro Gln Ser
                885                 890                 895
Ala Pro Ala Lys Glu Glu Asp Gln Gln Ser Phe Ser Glu Gly Thr Asp
            900                 905                 910
```

-continued

```
Ser Ala Ser Val Ala Asp Val Pro Ile Leu Gln Asp Ala Glu Asp Pro
        915                 920                 925

Phe Asn Glu Lys Ala Lys Gly Glu Ser Gly Asp Gly Ser Gly Phe Glu
        930                 935                 940

Ala Asn Phe Glu Ala Asn Phe Asp Ala Asn Phe Asp Asp Ala Phe Ala
945                 950                 955                 960

Gly Ser Gly Gly Gly Gly Gly Gly Gly Gly Gly Gly Gly Glu Gln Ser
                965                 970                 975

Asn Glu Leu Asp Ile Asn Gly Glu Ala Ala Gly Glu Ala Val Val Ser
        980                 985                 990

Gly Ser Ala Ala Gly Asp Glu Asp Ile Glu Ala Pro Lys Gln Val Val
        995                 1000                1005

Gly Gly Arg Ala Ser Ile Pro Glu Glu Leu Asp Ser Asn Gln Leu Ala
    1010                1015                1020

His Tyr His Glu His Glu Ile Tyr Tyr Val Asp Tyr Ser His Gly Gln
1025                1030                1035                1040

Leu

<210> SEQ ID NO 17
<211> LENGTH: 745
<212> TYPE: PRT
<213> ORGANISM: Drosophila melanogaster

<400> SEQUENCE: 17

Met Ala Tyr Ile Leu Lys Ala Thr Lys Cys Pro Thr Asp Glu Leu Ser
1               5                   10                  15

Leu Thr Asn Arg Ala Ile Val Asn Val Gly Asp Phe Pro Glu Glu Ile
            20                  25                  30

Lys Tyr Ala Asp Ile Ser Pro Ala Pro Gly Gln His Phe Ile Phe Ala
        35                  40                  45

Leu Glu Lys Thr Val Glu Val Pro Ser Gly Tyr Val Gly Phe Ser Leu
    50                  55                  60

Val Gln Arg Lys Trp Ala Met Val Ser Ile Asn Gln Glu Leu Glu Val
65                  70                  75                  80

Arg Pro Tyr Arg Phe Asp Ala Ser Ser Asp Val Ile Thr Cys Val Ser
                85                  90                  95

Phe Glu Thr Asp Phe Leu Gln Lys Lys Thr Val Ser Gln Glu Pro Tyr
            100                 105                 110

Asp Ser Asp Gln Met Ala Lys Glu Phe Ile Met Gln Phe Ala Gly Met
        115                 120                 125

Ala Leu Thr Val Gly Gln Ser Leu Val Phe Asn Phe Lys Asp Lys Lys
    130                 135                 140

Leu Leu Gly Leu Ala Val Lys Ser Leu Glu Ala Ile Asp Pro Lys Ser
145                 150                 155                 160

Leu Gly Glu Gly Lys Asp Thr Ala Met Arg Asn Val Arg Phe Gly Arg
                165                 170                 175

Ile Leu Gly Asn Thr Val Val Gln Phe Glu Lys Ala Glu Asn Ser Ser
            180                 185                 190

Leu Asn Leu Gln Gly Lys Ser Lys Gly Lys Val Val Arg Gln Ser Ile
        195                 200                 205

Ile Asn Pro Asp Trp Asp Phe Gly Lys Met Gly Ile Gly Gly Leu Asp
    210                 215                 220

Lys Glu Phe Asn Ser Ile Phe Arg Arg Ala Phe Ala Ser Arg Val Phe
225                 230                 235                 240
```

-continued

Pro Pro Glu Leu Val Glu Gln Leu Gly Cys Lys His Val Lys Gly Ile
            245                 250                 255

Leu Leu Tyr Gly Pro Gly Thr Gly Lys Thr Leu Met Ala Arg Gln
        260                 265                 270

Ile Gly Thr Met Leu Asn Ala Arg Glu Pro Lys Ile Val Asn Gly Pro
        275                 280                 285

Gln Ile Leu Asp Lys Tyr Val Gly Ser Glu Ala Asn Val Arg Arg
    290                 295                 300

Leu Phe Ala Glu Ala Glu Glu Glu Lys Arg Leu Gly Pro Asn Ser
305                 310                 315                 320

Gly Leu His Ile Ile Ile Phe Asp Glu Ile Asp Ala Ile Cys Lys Gln
                325                 330                 335

Arg Gly Ser Val Ala Gly Asn Ser Gly Val His Asp Thr Val Val Asn
            340                 345                 350

Gln Leu Leu Thr Lys Ile Asp Gly Val Asp Gln Leu Asn Asn Ile Leu
            355                 360                 365

Val Ile Gly Met Thr Asn Arg Arg Asp Met Ile Asp Glu Ala Leu Leu
    370                 375                 380

Arg Pro Gly Arg Leu Glu Val Gln Met Glu Ile Ser Leu Pro Asn Glu
385                 390                 395                 400

Gln Gly Arg Val Gln Ile Leu Asn Ile His Thr Lys Arg Met Arg Glu
                405                 410                 415

Phe Asn Lys Ile Asn Asp Asp Val Asp Asn Lys Glu Ile Ala Ala Leu
            420                 425                 430

Thr Lys Asn Phe Ser Gly Ala Glu Leu Glu Gly Leu Val Arg Ala Ala
        435                 440                 445

Gln Ser Ser Ala Met Asn Arg Leu Ile Lys Ala Asp Ala Lys Val Thr
    450                 455                 460

Val Asp Pro Glu Ala Met Glu Lys Leu Lys Val Asn Arg Asp Asp Phe
465                 470                 475                 480

Leu His Ser Leu Glu His Asp Ile Lys Pro Ala Phe Gly Thr Ala Gln
                485                 490                 495

Glu Ile Leu Asp Asn Met Leu Ala Arg Gly Val Ile Asn Trp Gly Ala
            500                 505                 510

Pro Val Ser Asn Leu Leu Glu Asp Gly Met Leu Tyr Val Gln Gln Ala
        515                 520                 525

Lys Ala Pro Glu Ser Ser Gly Leu Val Ser Val Leu Ala Gly Ala
    530                 535                 540

Pro Asn Ser Gly Lys Thr Ala Leu Ala Ala Gln Leu Ala Lys Met Ser
545                 550                 555                 560

Asp Phe Pro Phe Val Lys Val Cys Ser Pro Glu Asp Met Val Gly Tyr
                565                 570                 575

Thr Glu Ser Ala Lys Cys Leu His Ile Arg Lys Ile Phe Asp Asp Ala
            580                 585                 590

Tyr Arg Ser Met Leu Ser Cys Ile Val Val Asp Asn Val Glu Arg Leu
        595                 600                 605

Leu Asp Tyr Gly Ser Ile Gly Pro Arg Tyr Ser Asn Met Thr Leu Gln
    610                 615                 620

Ala Leu Leu Val Leu Leu Lys Lys Gln Pro Pro Lys Gly Arg Lys Leu
625                 630                 635                 640

Leu Ile Leu Cys Thr Ser Ser Arg Arg Glu Val Leu Glu Glu Met Glu
                645                 650                 655

Met Leu Thr Ala Phe Thr Ser Val Leu His Val Pro Asn Leu Ser Lys

```
                      660                 665                 670
Pro Asp His Val Leu Ala Val Leu Glu Asn Thr Asp Ile Phe Ser Lys
            675                 680                 685

Gly Glu Ile Gln Ala Ile Gly Lys Lys Met Ala Gly Lys Arg Val Phe
        690                 695                 700

Ile Gly Ile Lys Lys Leu Leu Gly Leu Ile Asp Met Ala Arg Gln Thr
705                 710                 715                 720

Glu Gln Ser Gln Arg Ala Ile Lys Phe Leu Ser Lys Met Glu Glu Glu
                725                 730                 735

Gly Gly Leu Asp Met Val Ala Arg Gln
            740                 745

<210> SEQ ID NO 18
<211> LENGTH: 2131
<212> TYPE: PRT
<213> ORGANISM: Drosophila melanogaster

<400> SEQUENCE: 18

Met Thr Glu Asp Ser Asp Ser Ile Ser Glu Glu Arg Ser Leu Phe
1               5                  10                  15

Arg Pro Phe Thr Arg Glu Ser Leu Val Gln Ile Glu Gln Arg Ile Ala
            20                  25                  30

Ala Glu His Glu Lys Gln Lys Glu Leu Glu Arg Lys Arg Ala Glu Gly
        35                  40                  45

Glu Val Leu Ile Tyr Cys Cys Pro Asn His Ser Val Gln Ile Arg Tyr
    50                  55                  60

Asp Asp Glu Asp Glu Asp Glu Gly Pro Gln Pro Asp Pro Thr Leu Glu
65                  70                  75                  80

Gln Gly Val Pro Ile Pro Val Arg Leu Gln Gly Ser Phe Pro Pro Glu
                85                  90                  95

Leu Ala Ser Thr Pro Leu Glu Asp Ile Asp Pro Tyr Tyr Ser Asn Val
            100                 105                 110

Leu Thr Phe Val Val Ser Lys Gly Lys Asp Ile Phe Arg Phe Ser
        115                 120                 125

Ala Ser Lys Ala Met Trp Met Leu Asp Pro Phe Asn Pro Ile Arg Arg
    130                 135                 140

Val Ala Ile Tyr Ile Leu Val His Pro Leu Phe Ser Leu Phe Ile Ile
145                 150                 155                 160

Thr Thr Ile Leu Val Asn Cys Ile Leu Met Ile Met Pro Thr Thr Pro
                165                 170                 175

Thr Val Glu Ser Thr Glu Val Ile Phe Thr Gly Ile Tyr Thr Phe Glu
            180                 185                 190

Ser Ala Val Lys Val Met Ala Arg Gly Phe Ile Leu Cys Pro Phe Thr
        195                 200                 205

Tyr Leu Arg Asp Ala Trp Asn Trp Leu Asp Phe Val Val Ile Ala Leu
    210                 215                 220

Ala Tyr Val Thr Met Gly Ile Asp Leu Gly Asn Leu Ala Ala Leu Arg
225                 230                 235                 240

Thr Phe Arg Val Leu Arg Ala Leu Lys Thr Val Ala Ile Val Pro Gly
                245                 250                 255

Leu Lys Thr Ile Val Gly Ala Val Ile Glu Ser Val Lys Asn Leu Arg
            260                 265                 270

Asp Val Ile Ile Leu Thr Met Phe Ser Leu Ser Val Phe Ala Leu Met
        275                 280                 285
```

-continued

```
Gly Leu Gln Ile Tyr Met Gly Val Leu Thr Gln Lys Cys Ile Lys Lys
    290                 295                 300

Phe Pro Leu Asp Gly Ser Trp Gly Asn Leu Thr Asp Glu Asn Trp Asp
305                 310                 315                 320

Tyr His Asn Arg Asn Ser Ser Asn Trp Tyr Ser Glu Asp Glu Gly Ile
                325                 330                 335

Ser Phe Pro Leu Cys Gly Asn Ile Ser Gly Ala Gly Gln Cys Asp Asp
            340                 345                 350

Asp Tyr Val Cys Leu Gln Gly Phe Gly Pro Asn Pro Asn Tyr Gly Tyr
        355                 360                 365

Thr Ser Phe Asp Ser Phe Gly Trp Ala Phe Leu Ser Ala Phe Arg Leu
    370                 375                 380

Met Thr Gln Asp Phe Trp Glu Asp Leu Tyr Gln Leu Val Leu Arg Ala
385                 390                 395                 400

Ala Gly Pro Trp His Met Leu Phe Phe Ile Val Ile Phe Leu Gly
                405                 410                 415

Ser Phe Tyr Leu Val Asn Leu Ile Leu Ala Ile Val Ala Met Ser Tyr
            420                 425                 430

Asp Glu Leu Gln Lys Lys Ala Glu Glu Glu Ala Ala Glu Glu Glu
        435                 440                 445

Ala Ile Arg Glu Ala Glu Glu Ala Ala Ala Lys Ala Ala Lys Leu
450                 455                 460

Glu Glu Arg Ala Asn Ala Gln Ala Gln Ala Ala Asp Ala Ala Ala
465                 470                 475                 480

Ala Glu Glu Ala Ala Leu His Pro Glu Met Ala Lys Ser Pro Thr Tyr
                485                 490                 495

Ser Cys Ile Ser Tyr Glu Leu Phe Val Gly Gly Glu Lys Gly Asn Asp
            500                 505                 510

Asp Asn Asn Lys Glu Lys Met Ser Ile Arg Ser Val Glu Val Glu Ser
        515                 520                 525

Glu Ser Val Ser Val Ile Gln Arg Gln Pro Ala Pro Thr Thr Ala His
    530                 535                 540

Gln Ala Thr Lys Val Arg Lys Val Ser Thr Thr Ser Leu Ser Leu Pro
545                 550                 555                 560

Gly Ser Pro Phe Asn Ile Arg Arg Gly Ser Arg Ser Ser His Lys Tyr
                565                 570                 575

Thr Ile Arg Asn Gly Arg Gly Arg Phe Gly Ile Pro Gly Ser Asp Arg
            580                 585                 590

Lys Pro Leu Val Leu Ser Thr Tyr Gln Asp Ala Gln Gln His Leu Pro
        595                 600                 605

Tyr Ala Asp Asp Ser Asn Ala Val Thr Pro Met Ser Glu Glu Asn Gly
    610                 615                 620

Ala Ile Ile Val Pro Val Tyr Tyr Gly Asn Leu Gly Ser Arg His Ser
625                 630                 635                 640

Ser Tyr Thr Ser His Gln Ser Arg Ile Ser Tyr Thr Ser His Gly Asp
                645                 650                 655

Leu Leu Gly Gly Met Ala Val Met Gly Val Ser Thr Met Thr Lys Glu
            660                 665                 670

Ser Lys Leu Arg Asn Arg Asn Thr Arg Asn Gln Ser Val Gly Ala Thr
        675                 680                 685

Asn Gly Gly Thr Thr Cys Leu Asp Thr Asn His Lys Leu Asp His Arg
    690                 695                 700

Asp Tyr Glu Ile Gly Leu Glu Cys Thr Asp Glu Ala Gly Lys Ile Lys
```

-continued

```
            705                 710                 715                 720
His His Asp Asn Pro Phe Ile Glu Pro Val Gln Thr Gln Thr Val Val
                    725                 730                 735
Asp Met Lys Asp Val Met Val Leu Asn Asp Ile Ile Glu Gln Ala Ala
                740                 745                 750
Gly Arg His Ser Arg Ala Ser Asp Arg Gly Val Ser Val Tyr Tyr Phe
            755                 760                 765
Pro Thr Glu Asp Asp Asp Glu Asp Gly Pro Thr Phe Lys Asp Lys Ala
        770                 775                 780
Leu Glu Val Ile Leu Lys Gly Ile Asp Val Phe Cys Val Trp Asp Cys
785                 790                 795                 800
Cys Trp Val Trp Leu Lys Phe Gln Glu Trp Val Ser Leu Ile Val Phe
                805                 810                 815
Asp Pro Phe Val Glu Leu Phe Ile Thr Leu Cys Ile Val Val Asn Thr
                820                 825                 830
Met Phe Met Ala Met Asp His His Asp Met Asn Lys Glu Met Glu Arg
                835                 840                 845
Val Leu Lys Ser Gly Asn Tyr Phe Phe Thr Ala Thr Phe Ala Ile Glu
850                 855                 860
Ala Thr Met Lys Leu Met Ala Met Ser Pro Lys Tyr Tyr Phe Gln Glu
865                 870                 875                 880
Gly Trp Asn Ile Phe Asp Phe Ile Ile Val Ala Leu Ser Leu Leu Glu
                885                 890                 895
Leu Gly Leu Glu Gly Val Gln Gly Leu Ser Val Leu Arg Ser Phe Arg
                900                 905                 910
Leu Leu Arg Val Phe Lys Leu Ala Lys Ser Trp Pro Thr Leu Asn Leu
            915                 920                 925
Leu Ile Ser Ile Met Gly Arg Thr Met Gly Ala Leu Gly Asn Leu Thr
        930                 935                 940
Phe Val Leu Cys Ile Ile Ile Phe Ile Phe Ala Val Met Gly Met Gln
945                 950                 955                 960
Leu Phe Gly Lys Asn Tyr His Asp His Lys Asp Arg Phe Pro Asp Gly
                965                 970                 975
Asp Leu Pro Arg Trp Asn Phe Thr Asp Phe Met His Ser Phe Met Ile
            980                 985                 990
Val Phe Arg Val Leu Cys Gly Glu Trp Ile Glu Ser Met Trp Asp Cys
        995                 1000                1005
Met Tyr Val Gly Asp Val Ser Cys Ile Pro Phe Phe Leu Ala Thr Val
    1010                1015                1020
Val Ile Gly Asn Leu Val Val Leu Asn Leu Phe Leu Ala Leu Leu Leu
1025                1030                1035                1040
Ser Asn Phe Gly Ser Ser Ser Leu Ser Ala Pro Thr Ala Asp Asn Asp
                1045                1050                1055
Thr Asn Lys Ile Ala Glu Ala Phe Asn Arg Ile Gly Arg Phe Lys Ser
                1060                1065                1070
Trp Val Lys Arg Asn Ile Ala Asp Cys Phe Lys Leu Ile Arg Asn Lys
            1075                1080                1085
Leu Thr Asn Gln Ile Ser Asp Gln Pro Ser Gly Glu Arg Thr Asn Gln
        1090                1095                1100
Ile Ser Trp Ile Trp Ser Glu Gly Lys Gly Val Cys Arg Cys Ile Ser
1105                1110                1115                1120
Ala Glu His Gly Asp Asn Glu Leu Glu Leu Gly His Asp Glu Ile Leu
                1125                1130                1135
```

```
Ala Asp Gly Leu Ile Lys Lys Gly Ile Lys Glu Gln Thr Gln Leu Glu
        1140                1145                1150

Val Ala Ile Gly Asp Gly Met Glu Phe Thr Ile His Gly Asp Met Lys
        1155                1160                1165

Asn Asn Lys Pro Lys Lys Ser Lys Tyr Leu Asn Asn Ala Thr Asp Asp
1170                1175                1180

Asp Thr Ala Ser Ile Asn Ser Tyr Gly Ser His Lys Asn Arg Pro Phe
1185                1190                1195                1200

Lys Asp Glu Ser His Lys Gly Ser Ala Glu Thr Met Glu Gly Glu Glu
        1205                1210                1215

Lys Arg Asp Ala Ser Lys Glu Asp Leu Gly Leu Asp Glu Glu Leu Asp
        1220                1225                1230

Glu Glu Gly Glu Cys Glu Gly Pro Leu Asp Gly Asp Ile Ile Ile
        1235                1240                1245

His Ala His Asp Glu Asp Ile Leu Asp Glu Tyr Pro Ala Asp Cys Cys
        1250                1255                1260

Pro Asp Ser Tyr Tyr Lys Lys Phe Pro Ile Leu Ala Gly Asp Asp Asp
1265                1270                1275                1280

Ser Pro Phe Trp Gln Gly Trp Gly Asn Leu Arg Leu Lys Thr Phe Gln
        1285                1290                1295

Leu Ile Glu Asn Lys Tyr Phe Glu Thr Ala Val Ile Thr Met Ile Leu
        1300                1305                1310

Met Ser Ser Leu Ala Leu Ala Leu Glu Asp Val His Leu Pro Gln Arg
        1315                1320                1325

Pro Ile Leu Gln Asp Ile Leu Tyr Tyr Met Asp Arg Ile Phe Thr Val
        1330                1335                1340

Ile Phe Phe Leu Glu Met Leu Ile Lys Trp Leu Ala Leu Gly Phe Lys
1345                1350                1355                1360

Val Tyr Phe Thr Asn Ala Trp Cys Trp Leu Asp Phe Val Ile Val Met
        1365                1370                1375

Val Ser Leu Ile Asn Phe Val Ala Ser Leu Val Gly Ala Gly Gly Ile
        1380                1385                1390

Gln Ala Phe Lys Thr Met Arg Thr Leu Arg Ala Leu Arg Pro Leu Arg
        1395                1400                1405

Ala Met Ser Arg Met Gln Gly Met Arg Val Val Val Asn Ala Leu Val
        1410                1415                1420

Gln Ala Ile Pro Ser Ile Phe Asn Val Leu Leu Val Cys Leu Ile Phe
1425                1430                1435                1440

Trp Leu Ile Phe Ala Ile Met Gly Val Gln Leu Phe Ala Gly Lys Tyr
        1445                1450                1455

Phe Lys Cys Glu Asp Met Asn Gly Thr Lys Leu Ser His Glu Ile Ile
        1460                1465                1470

Pro Asn Arg Asn Ala Cys Glu Ser Glu Asn Tyr Thr Trp Val Asn Ser
        1475                1480                1485

Ala Met Asn Phe Asp His Val Gly Asn Ala Tyr Leu Cys Leu Phe Gln
        1490                1495                1500

Val Ala Thr Phe Lys Gly Trp Ile Gln Ile Met Asn Asp Ala Ile Asp
1505                1510                1515                1520

Ser Arg Glu Val Asp Lys Gln Pro Ile Arg Glu Thr Asn Ile Tyr Met
        1525                1530                1535

Tyr Leu Tyr Phe Val Phe Phe Ile Ile Phe Gly Ser Phe Phe Thr Leu
        1540                1545                1550
```

-continued

```
Asn Leu Phe Ile Gly Val Ile Ile Asp Asn Phe Asn Glu Gln Lys Lys
        1555                1560                1565

Lys Ala Gly Gly Ser Leu Glu Met Phe Met Thr Glu Asp Gln Lys Lys
        1570                1575                1580

Tyr Tyr Asn Ala Met Lys Lys Met Gly Ser Lys Lys Pro Leu Lys Ala
1585                1590                1595                1600

Ile Pro Arg Pro Arg Trp Arg Pro Gln Ala Ile Val Phe Glu Ile Val
                1605                1610                1615

Thr Asp Lys Lys Phe Asp Ile Ile Met Leu Phe Ile Gly Leu Asn
        1620                1625                1630

Met Phe Thr Met Thr Leu Asp Arg Tyr Asp Ala Ser Asp Thr Tyr Asn
        1635                1640                1645

Ala Val Leu Asp Tyr Leu Asn Ala Ile Phe Val Val Ile Phe Ser Ser
        1650                1655                1660

Glu Cys Leu Leu Lys Ile Phe Ala Leu Arg Tyr His Tyr Phe Ile Glu
1665                1670                1675                1680

Pro Trp Asn Leu Phe Asp Val Val Val Ile Leu Ser Ile Leu Gly
                1685                1690                1695

Leu Val Leu Ser Asp Ile Ile Glu Lys Tyr Phe Val Ser Pro Thr Leu
        1700                1705                1710

Leu Arg Val Val Arg Val Ala Lys Val Gly Arg Val Leu Arg Leu Val
        1715                1720                1725

Lys Gly Ala Lys Gly Ile Arg Thr Leu Leu Phe Ala Leu Ala Met Ser
        1730                1735                1740

Leu Pro Ala Leu Phe Asn Ile Cys Leu Leu Leu Phe Leu Val Met Phe
1745                1750                1755                1760

Ile Phe Ala Ile Phe Gly Met Ser Phe Phe Met His Val Lys Glu Lys
                1765                1770                1775

Ser Gly Ile Asn Asp Val Tyr Asn Phe Lys Thr Phe Gly Gln Ser Met
        1780                1785                1790

Ile Leu Leu Phe Gln Met Ser Thr Ser Ala Gly Trp Asp Gly Val Leu
        1795                1800                1805

Asp Ala Ile Ile Asn Glu Glu Ala Cys Asp Pro Pro Asp Asn Asp Lys
        1810                1815                1820

Gly Tyr Pro Gly Asn Cys Gly Ser Ala Thr Val Gly Ile Thr Phe Leu
1825                1830                1835                1840

Leu Ser Tyr Leu Val Ile Ser Phe Leu Ile Val Ile Asn Met Tyr Ile
                1845                1850                1855

Ala Val Ile Leu Glu Asn Tyr Ser Gln Ala Thr Glu Asp Val Gln Glu
        1860                1865                1870

Gly Leu Thr Asp Asp Asp Tyr Asp Met Tyr Tyr Glu Ile Trp Gln Gln
        1875                1880                1885

Phe Asp Pro Glu Gly Thr Gln Tyr Ile Arg Tyr Asp Gln Leu Ser Glu
        1890                1895                1900

Phe Leu Asp Val Leu Glu Pro Pro Leu Gln Ile His Lys Pro Asn Lys
1905                1910                1915                1920

Tyr Lys Ile Ile Ser Met Asp Ile Pro Ile Cys Arg Gly Asp Leu Met
                1925                1930                1935

Tyr Cys Val Asp Ile Leu Asp Ala Leu Thr Lys Asp Phe Phe Ala Arg
        1940                1945                1950

Lys Gly Asn Pro Ile Glu Glu Thr Gly Glu Ile Gly Glu Ile Ala Ala
        1955                1960                1965

Arg Pro Asp Thr Glu Gly Tyr Glu Pro Val Ser Ser Thr Leu Trp Arg
```

```
                1970              1975              1980
Gln Arg Glu Glu Tyr Cys Ala Arg Leu Ile Gln His Ala Trp Arg Lys
1985              1990              1995              2000

His Lys Ala Arg Gly Glu Gly Gly Ser Phe Glu Pro Asp Thr Asp
             2005              2010              2015

His Gly Asp Gly Gly Asp Pro Asp Ala Gly Asp Pro Ala Pro Asp Glu
             2020              2025              2030

Ala Thr Asp Gly Asp Ala Pro Ala Gly Gly Asp Gly Ser Val Asn Gly
             2035              2040              2045

Thr Ala Glu Gly Ala Ala Asp Ala Asp Glu Ser Asn Val Asn Ser Pro
    2050              2055              2060

Gly Glu Asp Ala Ala Ala Ala Ala Ala Ala Ala Ala Ala Ala Ala Ala
2065              2070              2075              2080

Ala Gly Thr Thr Thr Ala Gly Ser Pro Gly Ala Gly Ser Ala Gly Arg
             2085              2090              2095

Gln Thr Ala Val Leu Val Glu Ser Asp Gly Phe Val Thr Lys Asn Gly
             2100              2105              2110

His Lys Val Val Ile His Ser Arg Ser Pro Ser Ile Thr Ser Arg Thr
         2115              2120              2125

Ala Asp Val
   2130

<210> SEQ ID NO 19
<211> LENGTH: 1739
<212> TYPE: PRT
<213> ORGANISM: Drosophila melanogaster

<400> SEQUENCE: 19

Met Ala Phe Pro Tyr Ile Trp Ala Leu Leu Pro Leu Ile Cys Ser Ala
  1               5                  10                  15

Ser Gly Leu Ser Leu Pro Asn Met Thr Ser Thr Asp Ala Val Val Ala
             20                  25                  30

Gly Gly Gly Ile Leu Pro Ile Leu Val Ala Gly Asn Pro Gly Asn Leu
         35                  40                  45

Gly Ser Ser Asn Met Ser Leu Ser Gly Gly Gly Leu Ala Gly Ser
    50                  55                  60

Ser Thr Gly Gly Gln Ser Leu Pro Asp Thr Gly Gly Asn Ser Ala
 65                  70                  75              80

Gly Gly Ser Pro Ala Gly Gly Ser Gly Thr Gly Gly Gly Ser
             85                  90                  95

Asn Ser Gly Ile Ser Gly Asn Asn Ser Ala Met Ile Gln Gly Gln Lys
                100                 105                 110

Ser Asn Gln Tyr Glu Lys Cys Ala Gly Pro Gly Asp Pro Gly Pro Cys
            115                 120                 125

Lys Gln Tyr Ile Tyr Lys Trp Arg Tyr Glu Pro Thr Thr Asn Glu Cys
    130                 135                 140

Thr Asn Phe Ile Trp Gly Gly Cys Glu Gly Asn Pro Gln Asn Arg Phe
145                 150                 155                 160

Gly Thr Glu Ala Glu Cys Leu Phe His Cys Ile Gly Gly Pro His Thr
                165                 170                 175

Leu Pro Pro Phe Leu Gln Ser Thr Thr Arg Glu Pro Ser Thr Thr Glu
            180                 185                 190

Ser Ser Met Leu Leu Gly Leu Pro Tyr Thr Gln Ser Pro Ala Gln Ser
    195                 200                 205
```

```
Pro Asp Gly Met Gly Gly Ala Glu Gly Gly Asp Gly Thr Thr Pro Val
210                 215                 220
Pro Ile Glu Gln Arg Gly Pro Glu Leu Thr Phe Ala Glu Thr Gly Gln
225                 230                 235                 240
Gly Lys Thr Phe Ile Phe Ala Lys Asn Asn Thr Phe Ile Gln Met Asp
                245                 250                 255
Gly Asp Ile Ile Gln Thr Phe Gln Leu Arg Leu Cys Arg Glu Ile Ser
            260                 265                 270
Phe Gln Phe Arg Thr Arg Leu Pro His Gly Leu Leu Val Tyr His Asn
        275                 280                 285
Val Lys Asn Pro Asp Arg Ile Asn Leu Asp Pro Tyr Ala Leu Tyr Val
    290                 295                 300
Ile Val Glu Lys Gly Gln Leu Lys Val Val His Val Phe Gly Lys His
305                 310                 315                 320
Ser Thr Ser Val Thr Val Gly Glu Ser Leu Asn Arg Asp Glu Trp His
                325                 330                 335
Ser Val Met Val Arg Ile Asp Val His Gly Ala Arg Leu Ile Ala Arg
            340                 345                 350
Val Asp Asn Ser Gln Glu Glu Val Tyr Leu Lys Gly Leu Asn His Glu
        355                 360                 365
Tyr Asn Tyr Gly Val Ser Thr Asn Leu Pro Ser Val Leu Val Gly
    370                 375                 380
Gly Gly Leu Ser Ser Glu Glu Lys Leu His Gly Val Lys Tyr Ile Thr
385                 390                 395                 400
Glu Ser Phe Val Gly Cys Ile Arg Asn Val Val Leu Ser Ser Gly Lys
                405                 410                 415
Ala Ala Ser Asp Leu Leu Pro Ile Ala Pro Leu Val Ala Thr Lys His
            420                 425                 430
Glu Asn Val Asn Glu Gly Cys Ser Asp Met Cys Glu Ser Arg His Asn
        435                 440                 445
Leu Cys Phe Val Gly Ser Arg Cys Ile Asn His Tyr Gly Gly Ile Ser
    450                 455                 460
Cys Asp Cys Phe Gly Thr His Tyr Glu Gly His Cys Asp Ile Tyr
465                 470                 475                 480
Ser Asp Ile Ile Thr Leu Arg Gly Ala Ser Tyr Val Ser Tyr Arg Ile
                485                 490                 495
Tyr Asp Trp Lys Asp Arg Val His Ser Ser Thr Arg Arg Ile Ser Leu
            500                 505                 510
Met Phe Arg Thr Asn Phe Asp Ser Ala Leu Phe Tyr Ala Ser Gly
        515                 520                 525
Glu Ser Leu Lys His Gln Tyr Ile Ala Ala Ser Ile Lys Asn Gln Ser
    530                 535                 540
Val His Val Glu Met Asp Phe Gly Asp Asn Val Met Ser Thr Val Leu
545                 550                 555                 560
Thr Asp Asp Leu Thr Arg Gly Tyr Trp His Asn Leu Thr Ile Leu His
                565                 570                 575
Glu Gln Arg Thr Val Ser Ile Ile Leu Asp Gln Gln Lys Val Leu
            580                 585                 590
Glu Leu Pro Ala Thr Ala Ser Gly Asn Met Leu Phe Asp Pro Glu Ile
        595                 600                 605
Tyr Phe Gly Gly Pro Glu Leu His Lys Lys Gly Leu Ala Ser
    610                 615                 620
His Asn Asn Phe Val Gly Ser Leu Lys Tyr Val Tyr Tyr Asn Asp Ile
```

-continued

```
             625                 630                 635                 640
Ser Ile Leu Tyr Glu Leu Gln Arg Gly Asn Pro Lys Val His Tyr His
                 645                 650                 655
Gly Val Leu Glu Ala Glu Phe Val Glu Asn Val Asn Val Ile Pro
             660                 665                 670
Ile Thr Tyr Pro Phe Ala Thr Ser His Ile Trp Trp Pro Ile Asn His
             675                 680                 685
Ala Glu Glu Phe Asn Ile Lys Phe Asp Phe Arg Ser Ser Arg Pro Gly
             690                 695                 700
Ala Val Leu Ala Tyr Ser Asp Val Thr Thr Ser Ala Gly Asn Gly Phe
705                 710                 715                 720
Trp Glu Ile Arg Leu Thr Ser Asp Lys Leu Ser Phe Asp Leu Val Pro
                 725                 730                 735
Asp Val Asn Asn Asn Val Thr His Ser Thr Thr Ile Lys Ile Asn Arg
             740                 745                 750
Ala Thr Ser Trp His Ser Val Glu Leu Asp Tyr Lys Leu Gly Glu Ile
             755                 760                 765
Arg Phe Thr Val Asp Tyr Arg His Thr Leu Ser Gln Met Tyr Gly Leu
             770                 775                 780
Thr Phe Asn Ile Gly Asp Lys Leu Ile Ile Gly Ser Ser Leu Lys Ser
785                 790                 795                 800
Ala Ala Met Gly Leu Val Gly Cys Ile Arg Asp Ile Glu Ile Asn Gly
                 805                 810                 815
His Leu Ile Glu Pro Arg His Val Val Lys Thr Glu Arg Val Val Gly
             820                 825                 830
Glu Val Ala Leu Asp Asn Cys Asn Tyr Ile Asp Pro Cys Lys Arg Pro
             835                 840                 845
Asn Thr Cys Glu His Gly Gly Lys Cys Phe Val Lys Asp Asp Arg Val
850                 855                 860
Thr Cys Asp Cys Lys His Thr Gly Tyr Ile Gly Lys Asn Cys His Phe
865                 870                 875                 880
Thr Lys Tyr Arg Lys Thr Cys Glu Glu Leu Ala Leu Leu Gly Phe Thr
                 885                 890                 895
Lys Ser Asp Val Tyr Leu Ile Asp Ile Asp Gly Asn Gly Val Phe Pro
             900                 905                 910
Pro Ala His Val Lys Cys Asp Phe Gln Ser Leu Glu Asn Ala Thr Lys
             915                 920                 925
Thr Ile Val Glu His Asn Leu Pro Ser Gln Val Asp Val Arg Ser Ala
             930                 935                 940
Arg Glu Ser Asp Phe Ser Phe Asn Ile Arg Tyr Arg Glu Phe Ser Pro
945                 950                 955                 960
His Met Leu Gln Glu Leu Ile Ser His Ser Leu Tyr Cys Thr Gln Tyr
                 965                 970                 975
Ile Lys Tyr Asp Cys Tyr Arg Ala Gln Leu Glu Leu His Ser Ala Thr
             980                 985                 990
Trp Phe Thr Ser Ser Ala Lys Asn Leu Thr Val Asp Phe Leu Gly Asn
             995                 1000                1005
Val Lys Arg Gly Ala Cys Pro Cys Ser Val Asn Lys Thr Cys Val Asp
         1010                1015                1020
Pro Asn Gln Ser Cys Asn Cys Asp Val Lys Glu Asn Lys Trp Asn Ser
     1025                1030                1035                1040
Asp Glu Gly Tyr Tyr Gln Asp Pro Gln Ser Leu Gly Ile Thr Asn Met
                 1045                1050                1055
```

```
Tyr Phe Leu Gln Gln Lys Asp Met Asp Asp Glu Ala Gln Gly Arg Ile
            1060                1065                1070
Thr Leu Gly Pro Leu Glu Cys Val Glu Thr Asn Thr Gln Lys Tyr Val
        1075                1080                1085
Val Thr Phe Thr Thr Ser Gln Ser Tyr Ile Glu Val Pro Gly Trp Arg
    1090                1095                1100
Lys Gly Asp Ile Ala Phe Ser Phe Arg Thr Thr Gly Glu Lys Ala Ile
1105                1110                1115                1120
Leu Leu Phe Gln Pro Pro Ile Arg Pro His Tyr Pro Ser Phe Met Val
                1125                1130                1135
Ala Leu Thr Gly Asp Asp Gln Leu Thr Phe Thr Phe Thr Leu Ser Thr
            1140                1145                1150
Gly Thr Thr Arg Glu Leu Val Ile Asn Ser His Arg Arg Leu Asn Gly
        1155                1160                1165
Gly Glu Trp His Lys Ile Trp Ile Asp Tyr Asn Gln Tyr His Val Arg
    1170                1175                1180
Phe Met Ile Asn Thr Asp Tyr Gln Met Leu Asp Leu Leu Pro Glu Glu
1185                1190                1195                1200
Glu Phe Gly Pro Phe Glu Gly Ser Met Tyr Ile Gly Gly Ala Thr Phe
                1205                1210                1215
Asp Leu Leu Lys Lys Leu Ser Val Lys Ala Gly Leu Ile Gly Cys Phe
            1220                1225                1230
Arg Gly Leu Val Val Asn Gly Glu Ile Leu Asp Ile Tyr Ser Tyr Met
        1235                1240                1245
Ser Val His Leu Ser Glu Ile Ile Lys Asp Cys Lys Pro Ser Cys Val
    1250                1255                1260
Pro Ser Pro Cys Arg Asn Gly Ala Gln Cys Lys Glu Leu Trp Ser Ser
1265                1270                1275                1280
Phe Lys Cys Val Cys Asn Asn Pro Trp Ala His Ile Gly Glu Phe Cys
                1285                1290                1295
Glu Thr Asn Ile Asn Glu Lys Ala Leu Thr Phe Ile Asn Arg Glu Ser
            1300                1305                1310
Phe Leu Met Arg Asn Tyr Leu Ser Val Gly Ala Thr Pro Val Ile Leu
        1315                1320                1325
Met His Gly Ile Asn Gly Glu Arg Asp Val Leu Lys Gly Ile Leu Asn
    1330                1335                1340
Gln Asp Leu Leu Ile Asn Leu Arg Thr Tyr Asp Thr Asn Ala Leu Val
1345                1350                1355                1360
Leu Tyr Ala Asn Asp His Tyr Asn Asn Phe Val His Leu Tyr Ile Ser
                1365                1370                1375
Leu Asn Arg Glu Ile Val Phe Leu Tyr Asn Tyr Gly Asp Glu Ile Val
            1380                1385                1390
Asn Leu Thr Leu Leu Asp Asp Thr Leu Met Ala Ser Leu Lys Ser Ile
        1395                1400                1405
Gln Val Ala Ile Val Arg Gly Glu Gln Glu Thr Arg Met His Val Asn
    1410                1415                1420
Glu His Ser Val Ser Ile Asp Arg Gly Thr Leu Leu Leu Asp Glu Tyr
1425                1430                1435                1440
Ala Asn Lys Pro Trp Ser Asn Pro Glu Lys Gly Lys Leu Arg Pro Asn
                1445                1450                1455
Val Asp Ala Pro Ala Leu Glu Gly Tyr Ile Gly Cys Val Arg Gly Leu
            1460                1465                1470
```

-continued

Lys Ile Gly Ala Gln Leu Ile Asp Leu Ala Asp Ile Asn Glu Arg Asn
        1475                1480                1485

Ile Ala Pro Thr Gln Glu Gly Val Leu Pro Asn Cys Gln Ile Lys Cys
        1490                1495            1500

Asp Ala Glu Pro Cys Lys Asn Gly Gly Thr Cys Gln Glu His Phe Ala
1505                1510                1515                1520

Glu Gln Leu Ser Thr Cys Asp Cys Glu His Thr Ser Phe Leu Gly Glu
        1525                1530                1535

Phe Cys Ser Glu Glu Lys Gly Ala Asp Phe Ser Gly Glu Ser Thr Leu
        1540                1545                1550

Gln Arg Lys Phe Glu Leu Pro Gly Thr Gly Arg Val Asp Tyr Val Arg
        1555                1560                1565

Leu Gln Leu Ala Phe Ser Ser Phe Asp Leu Arg Arg Ala Asn Arg Ile
        1570                1575                1580

Met Leu Leu Met Gln Thr Glu Ala Glu Arg Ser Tyr Tyr Leu Leu Leu
1585                1590                1595                1600

Ala Ile Thr Ser Asp Gly Tyr Leu Gln Leu Glu Glu Asp Arg Asp Asn
        1605                1610                1615

Gly Gln Thr Val Gly Ala Arg Ile Asp Arg Asn Phe Leu Asn Ser Ala
        1620                1625                1630

Arg His Ser Val Tyr Tyr Val Arg Asn Gly Thr Gln Ser Gln Leu Phe
        1635                1640                1645

Ile Asp Arg Glu Gln Val Pro Leu Ser Glu Phe Ala Ala Arg Val Leu
        1650                1655                1660

Thr Thr Gly Gly Asp Ala Gly Ser Asn Arg Val Gln Ile Gly Gly Ile
1665                1670                1675                1680

Asn Ser Thr Asp Ser Arg Phe Ala Val Phe Lys Ser Tyr Ser Gly Cys
        1685                1690                1695

Leu Ser Ser Glu Cys Arg Lys Phe His Ala Arg Leu Pro Leu Ile Ser
        1700                1705                1710

Phe Arg Ser His Gln Val Thr Tyr Pro Phe Ala Pro Phe Ala Lys Lys
        1715                1720                1725

Lys Lys Ile Glu Ile Lys Tyr Thr Glu Arg Ile
        1730                1735

<210> SEQ ID NO 20
<211> LENGTH: 985
<212> TYPE: PRT
<213> ORGANISM: Drosophila melanogaster

<400> SEQUENCE: 20

Met Val Gly Gln Leu Gln Gly Gly Gln Ala Ala Gly Gln Gln Gln Gln
1               5                   10                  15

Gln Gln Gln Ala Thr Gln Gln Gln Gln His Ser Lys Gln Gln Gln Gln
            20                  25                  30

Gln Gln Gln Gln Gln Gln Gln Leu Gln Leu Lys Gln His Gln Gln
        35                  40                  45

Gln Gln Gln Asp Ile Leu Tyr Gln Gln His Asn Glu Ala Ile Ala Ile
    50                  55                  60

Ala Arg Gly Leu Gln Ala Ala Thr Pro Ala Asp Ile Gly Asp Asn Gln
65                  70                  75                  80

Pro Tyr Tyr Asp Thr Ser Gly Asn Val Asp Trp Glu Arg Ala Met Gly
            85                  90                  95

Ala Gly Gly Ala Gly Ala Tyr Gly Gly Ile Gly Ile Gly Ser Leu Pro
            100                 105                 110

-continued

```
Ala Ala Gly Gly Ala Ala Tyr His Leu Gly Pro Ala Asn Pro Ala Gly
            115                 120                 125

Leu Val Ser Arg His Leu Asp Tyr Gly Asp Gly His Leu Ala Gly
    130                 135                 140

Pro Ser Ala Gly Leu Pro Ala Gly Ala Val Gly Ser Gly Ala Gly Ala
145                 150                 155                 160

Gly Ala Gly Ala Gly Ala Ser Val Thr Gly Ser Gly Ser Gly Ala Gly
                165                 170                 175

Thr Gly Thr Gly Thr Gly Ala Gly Ser Gly Ser Gly Ser Gly Ala Ala
                180                 185                 190

Gly Lys Glu Val Arg Tyr Ala Pro Phe Pro Val Ala Ser Pro Thr His
            195                 200                 205

Ser Ile Pro Thr Thr Ser Gln Gln Ile Val Gly Ser Val Gly Gly Val
    210                 215                 220

Gly Val Gly Gly Ala Ser Ser Gln Ser Ile Ser Gly Gly Val Pro Thr
225                 230                 235                 240

His Ser Gln Ser Asn Thr Thr Gly Ala Leu Gln Arg Thr His Ser Arg
                245                 250                 255

Ser Met Ser Ser Ile Pro Pro Glu Pro Phe Met Ile Ala Gln Ser
                260                 265                 270

Lys Ala Val Asn Ser Arg Val Ser Ile Asn Val Gly Gly Val Arg His
            275                 280                 285

Glu Val Leu Trp Arg Thr Leu Glu Arg Leu Pro His Thr Arg Leu Gly
    290                 295                 300

Arg Leu Arg Glu Cys Thr Thr His Glu Ala Ile Val Glu Leu Cys Asp
305                 310                 315                 320

Asp Tyr Ser Leu Ala Asp Asn Glu Tyr Phe Phe Asp Arg His Pro Lys
                325                 330                 335

Ser Phe Ser Ser Ile Leu Asn Phe Tyr Arg Thr Gly Lys Leu His Ile
                340                 345                 350

Val Asp Glu Met Cys Val Leu Ala Phe Ser Asp Asp Leu Glu Tyr Trp
            355                 360                 365

Gly Val Asp Glu Leu Tyr Leu Glu Ser Cys Cys Gln His Lys Tyr His
    370                 375                 380

Gln Arg Lys Glu Asn Val His Glu Glu Met Arg Lys Glu Ala Glu Ser
385                 390                 395                 400

Leu Arg Gln Arg Asp Glu Glu Glu Phe Gly Glu Gly Lys Phe Ser Glu
                405                 410                 415

Tyr Gln Lys Tyr Leu Trp Glu Leu Leu Glu Lys Pro Asn Thr Ser Phe
            420                 425                 430

Ala Ala Arg Val Ile Ala Val Ile Ser Ile Leu Phe Ile Val Leu Ser
            435                 440                 445

Thr Ile Ala Leu Thr Leu Asn Thr Leu Pro Gln Leu Gln His Ile Asp
    450                 455                 460

Asn Gly Thr Pro Gln Asp Asn Pro Gln Leu Ala Met Val Glu Ala Val
465                 470                 475                 480

Cys Ile Thr Trp Phe Thr Leu Glu Tyr Ile Leu Arg Phe Ser Ala Ser
                485                 490                 495

Pro Asp Lys Trp Lys Phe Lys Gly Gly Leu Asn Ile Ile Asp Leu
                500                 505                 510

Leu Ala Ile Leu Pro Tyr Phe Val Ser Leu Phe Leu Leu Glu Thr Asn
            515                 520                 525
```

-continued

Lys Asn Ala Thr Asp Gln Phe Gln Asp Val Arg Arg Val Gln Val
    530                 535                 540

Phe Arg Ile Met Arg Ile Leu Arg Val Leu Lys Leu Ala Arg His Ser
545                 550                 555                 560

Thr Gly Leu Gln Ser Leu Gly Phe Thr Leu Arg Asn Ser Tyr Lys Glu
                565                 570                 575

Leu Gly Leu Leu Met Leu Phe Leu Ala Met Gly Val Leu Ile Phe Ser
            580                 585                 590

Ser Leu Ala Tyr Phe Ala Glu Lys Asp Glu Lys Asp Thr Lys Phe Val
        595                 600                 605

Ser Ile Pro Glu Ala Phe Trp Trp Ala Gly Ile Thr Met Thr Thr Val
    610                 615                 620

Gly Tyr Gly Asp Ile Cys Pro Thr Thr Ala Leu Gly Lys Val Ile Gly
625                 630                 635                 640

Thr Val Cys Cys Ile Cys Gly Val Leu Val Val Ala Leu Pro Ile Pro
                645                 650                 655

Ile Ile Val Asn Asn Phe Ala Glu Phe Tyr Lys Asn Gln Met Arg Arg
                660                 665                 670

Glu Lys Ala Leu Lys Arg Arg Glu Ala Leu Asp Arg Ala Lys Arg Glu
            675                 680                 685

Gly Ser Ile Val Ser Phe His His Ile Asn Leu Lys Asp Ala Phe Ala
690                 695                 700

Lys Ser Met Asp Leu Ile Asp Val Ile Asp Thr Gly Lys Gln Thr
705                 710                 715                 720

Asn Val Val His Pro Lys Gly Lys Arg Gln Ser Thr Pro Asn Ile Gly
                725                 730                 735

Arg Gln Thr Leu Asp Val Gln Ser Ala Pro Gly His Asn Leu Ser Gln
            740                 745                 750

Thr Asp Gly Asn Ser Thr Glu Gly Glu Ser Thr Ser Gly Arg Asn Pro
        755                 760                 765

Ala Thr Thr Gly Thr Gly Cys Tyr Lys Asn Tyr Asp His Val Ala Asn
    770                 775                 780

Leu Arg Asn Ser Asn Leu His Asn Arg Arg Gly Ser Ser Ser Glu Gln
785                 790                 795                 800

Asp Ala Val Pro Pro Tyr Ser Phe Asp Asn Pro Asn Ala Arg Gln Thr
                805                 810                 815

Ser Met Met Ala Met Glu Ser Tyr Arg Arg Glu Gln Gln Ala Leu Leu
            820                 825                 830

Gln Gln Gln Gln Gln Gln Gln Gln Met Leu Gln Met Gln Gln Ile
        835                 840                 845

Gln Gln Lys Ala Pro Asn Gly Asn Gly Ala Thr Gly Gly Val
    850                 855                 860

Ala Asn Asn Leu Ala Met Val Ala Ala Ser Ala Ala Thr Ala Val
865                 870                 875                 880

Ala Thr Ala Thr Asn Ala Ser Asn Ala Ser Asn Thr Ala Pro Gly Ser
                885                 890                 895

Glu Gly Ala Glu Gly Gly Gly Asp Gly Asp Gly Gly Val Asp Asp
            900                 905                 910

Asp Asn Leu Ser Gln Ala Lys Gly Leu Pro Ile Gln Met Met Ile Thr
        915                 920                 925

Pro Gly Glu Val Ala Glu Leu Arg Arg Gln Val Ala Leu Glu Asn Leu
    930                 935                 940

Gln Asn Gln Arg Met Asp Asn Leu Glu Gln Asp Val Pro Val Glu Phe

```
                945                 950                 955                 960
            Glu Cys Cys Phe Cys Thr Thr Lys Gly Leu Pro Gly Cys His Gly Glu
                            965                 970                 975
            Cys Ile Pro Leu Arg Ala Asn Ser Val
                        980                 985
```

NEURODEGENERATION MUTANTS, METHOD FOR IDENTIFYING SAME, AND METHOD FOR SCREENING NEUROPROTECTIVE AGENTS

STATEMENT REGARDING FEDERALLY SPONSORED RESEARCH OR DEVELOPMENT

This invention was made with United States Government support awarded by the following agency: NIH Grant No. NS15390. The United States has certain rights in this invention.

CROSS-REFERENCE TO RELATED APPLICATION

Not applicable.

BACKGROUND OF THE INVENTION

The cellular and molecular mechanisms underlying age-dependent neurodegeneration seen in metazoans from worms to humans are poorly understood. Neurodegeneration is largely genetic in origin and often results from a single gene defect. (reviewed in FORTINI and BONINI 2000; HEINTZ and ZOGHBI 2000; FEANY 2000; FORMAN et al. 2000; GOEDERT 2001; SIPIONE and CATTANEO 2001; MACCIONI et al. 2001). Human neurodegenerative illnesses, such as Amyotropic Lateral Sclerosis (ALS), Huntington disease, Parkinson disease, and Alzheimer disease are characterized by progressive behavioral deficits, premature death and, in some cases, profound cognitive impairment. Onset of the symptoms of these diseases correlates with the appearance of neuropathology. Mutations that underlie some forms of these diseases are known, but a general understanding of the molecular mechanisms required for maintaining neuronal viability are not understood.

A great demand exists for therapeutic interventions for neurodegenerative diseases, particularly for administration to elderly subjects. Notwithstanding the great demand, few if any drugs are available to reduce age-related neurodegeneration. At the heart of this lack of therapeutic agents is the lack of adequate screening assays for novel therapeutic interventions. Typically, neuroblast-derived cell lines in culture are exposed to putative agents and agents that extend the life in culture are selected for further investigation. What is missing is an efficient in vivo technology for use as a primary screen or for confirming effectiveness of putative neuroprotective agents.

Human neurodegenerative conditions can be modeled in *Drosophila*. In some cases, human proteins, such as alpha-synuclein and tau, are expressed in *Drosophila* and cause neurodegenerative syndromes having phenotypic properties similar to those of Parkinson and Alzheimer diseases, respectively. Likewise, flies expressing human Huntingtin containing expanded triplet repeats develop neuropathological defects reminiscent of human Huntington disease. Using this model system, various suppressor mutations have been isolated. It has further been determined that onset of neurodegeneration in flies can be suppressed by overexpressing human hsp70. Accordingly, it appears that *Drosophila* can be instrumental in uncovering key mechanisms of general significance in the field of neurodegenerative disorders.

Additionally, *Drosophila* have been screened for single gene mutations that cause neurodegeneration. Mutants such as drop dead, swiss cheese, eggroll, spongecake, and bubblegum have moderate to markedly reduced lifespans and associated neuropathology including vacuolization and accumulation of multi-lamellar cell bodies. These neuropathologies are similar to those seen in patients having Tay-Sachs and Creutzfeldt-Jakob diseases.

Still, the number of neurodegeneration mutants is quite small and additional neurodegeneration mutants are of interest. Such mutants not only help in deciphering basic neurodegeneration biology, but can also serve as convenient and inexpensive models both for genetic therapies and for screening putative neuroprotective agents. It is, of course, difficult to ascertain which strains of *Drosophila* exhibit neurodegeneration. It is impractical to screen all strains and mutants for neurodegeneration and the art lacks a principled basis upon which one would select candidates a priori. Prior efforts have examined flies on the basis of a defect in phototaxis or reduced life span. (HEISENBERG and BOHL, 1979; HEISENBERG 1979; COOMBE and HEISENBERG 1986; BUCHANAN and BENZER 1993; MIN and BENZER 1997; KRETZSCHMAR et al. 1997). For example, Min and Benzer, 1997 examined five thousand mutagenized lines and isolated sixty mutant lines having reduced lifespan. Of the sixty mutants, two (0.4% of the mutagenized lines examined) exhibited neurodegeneration. Screening for mutant lines having reduced life span presents at least two inherent disadvantages, namely the substantial time required to ascertain a shortened life span and the low incidence in such mutants of neurodegeneration. A more targeted and efficient approach to screening for neurodegeneration mutants in *Drosophila* is desired.

Previous studies have established a connection between neuronal dysfunction and neurodegeneration in some species. Some neurodegenerative mutants affect genes that encode ion channels and neurotransmitter receptors. Weaver (wv), lurcher (Lc), and tottering (tg) were identified in mice on the basis of locomotor behavior defects and contain mutations in genes that encode ion channels and neurotransmitter receptors. Studies of these mutants have demonstrated an important connection between aberrant neuronal signaling properties and neurodegeneration (MURTOMAKI et al. 1995; NORMAN et al. 1995; FLETCHER et al. 1996; ZUO et al. 1997). The connection is also established in the worm sensory system (HALL et al. 1997). An indirect connection between neurodegeneration and ion channels is seen in *Drosophila* dADAR mutants which exhibit extensive neurodegeneration arising from lack of an enzyme essential for adenosine to inosine type editing of pre-mRNAs that encode several *Drosophila* ion channels. Notably, dADAR null mutants undergo extensive neurodegeneration (PALLADINO et al. 2000a).

This application also describes various mutations in the alpha subunit of $Na^+/K^+$ ATPase pumps (sodium pumps) that asymmetrically distribute $Na^+$ and $K^+$ ions to form ion gradients across the plasma membrane of cells. These ion gradients determine the membrane resting potential and excitability of cells and drive many important secondary processes. Without such ion gradients, many essential functions, including electrical signaling in the nervous system, are not possible. Many sodium pump isozymes exist, are highly conserved evolutionarily, and are widely expressed in animal tissues. In neurons, sodium pumps generate and maintain the membrane potential after extensive $Na^+$ influx enabling continued generation of action potentials. Not surprisingly, sodium pumps are extensively regulated in vivo (reviewed in THERIN and BOLSTEIN, 2000).

Sodium pumps have at least two essential subunits, alpha and beta. The alpha subunit of the *Drosophila* $Na^+/K^+$ ATPase (ATPalpha) is a large protein (>110 kDa) with multiple transmembrane domains and an ATP-dependent catalytic activity. A version of *Drosophila* ATPalpha is available in Genbank at Accession No. XP-081160, presented herein as SEQ ID NO:1. Mutations and reversions described herein are defined relative to the ATPalpha amino acid sequence disclosed in Accession No. XP-081160 and are not separately presented. It is understood that the skilled artisan can readily understand the complete sequences of mutants and reversions from the information presented in the specification. The beta subunit has a single transmembrane domain and may be involved in pump maturation, membrane localization and functional properties of $Na^+/K^+$ ATPases.

Studies characterizing the functions and importance of $Na^+/K^+$ ATPase proteins in vivo in other animals are limited but suggest that normal neural development and maintenance requires proper $Na^+/K^+$ ATPase function. One study of $Na^+/K^+$ ATPase loss-of-function eat-6 mutations in the nematode established a link between pharyngeal function and sodium pump activity. Null mutations of the mouse $Na^+/K^+$ ATPase beta2 subunit cause neural cell degeneration, apoptotic photoreceptor cell death, and death late in development.

The importance of $Na^{+/K+}$ ATPase function has also been suggested by widespread expression in metazoan tissues, striking evolutionary conservation, and involvement in many essential processes including nutrient absorption, nephritic function and signaling in the nervous system. Many studies suggest a pathophysiological connection between the biochemical function of these important proteins and human neural diseases including bipolar disorder, seizures and neurodegenerative conditions, namely spongiform encephalopathies, with manifestations similar to those caused by prion diseases, namely Kuru, Crutzfeld-Jakob disease, and Gerstmann-Straussler-Scheinker syndrome (reviewed by MOBASHERI et al, 2000).

$Na^{+/K+}$ ATPase function is also implicated in cardiac hypertrophy, hypertension, renal dysfunction, bipolar mood disorder, and spongiform encephalopathies. Somewhat surprisingly, no direct mutation of $Na^{+/K+}$ ATPase alpha has been identified as the cause of neural disease.

Among conditional paralytic mutants, mutations are known to cause neuronal dysfunction by disrupting polynucleotides that encode electrical signaling proteins. One bang-sensitive paralytic mutation and several lethal p element insertions have been mapped to ATPalpha (SCHUBIGER, 1994), (FENG, 1997). Additionally, transgenic ATPalpha having specific modifications at a phosphorylation site required during ATP hydrolysis causes bang-sensitive paralysis and, in some cases, death (SUN, 2001).

No association between neurodegeneration and mutations in $Na^{+/K+}$ ATPase alpha has been reported, although loss of $Na^{+/K+}$ ATPase function can cause neuropathological effects (reviewed in Beal, 1993; Lees, 1993). These neuropathological effects are seen after administering $Na^{+/K+}$ ATPase inhibitors or in the presence of mutations that affect $Na^+/K^+$ ATPase beta subunits. In addition, inherited defects associated with reduced $Na^{+/K+}$ ATPase activity have been linked to neonatal status convulsivus, spongiform encephalopathy (RENKAWEK et al, 1992).

BRIEF SUMMARY OF THE INVENTION

A novel method is disclosed for identifying neurodegeneration mutants in *Drosophila* and specific mutations in the nucleic acid of the neurodegeneration mutants and polypeptides encoded by the mutants. Neurodegeneration mutants are advantageously and efficiently obtained in a selection and screening method, in which a selected collection of temperature-sensitive paralytic mutants or bang-sensitive paralytic mutants are screened for neurodegeneration as described herein. The high incidence of neurodegeneration mutants found among temperature-sensitive paralytic mutants and bang-sensitive paralytic mutants suggests that perturbation of neuronal signaling pathways can contribute to neurodegeneration.

In accord with one aspect of the invention, the inventors herein demonstrate that a collection of mutants exhibiting aberrant behaviors associated with altered or impaired neural function are enriched in mutants that exhibit characteristic neurodegeneration. In a related aspect, therefore, one principle of the invention is the novel appreciation that the task of identifying neurodegeneration mutants is eased appreciably by selecting as a starting material for use in the method of the invention a collection of such behavioral mutants. The skilled artisan will appreciate that the likelihood of identifying a neurodegeneration mutant in the method of the invention increases with an increase in the number of screened behavioral mutants.

In particular, temperature-sensitive paralytic behavioral mutants and bang-sensitive paralytic behavioral mutants are advantageously used as starting materials to be screened in the method of the invention. Mutants to be screened in the method of the invention can include, but need not be limited to mutants carrying non-wild-type ion channel structural genes, ion channel regulatory genes and genes affecting synaptic transmission machinery. Many temperature-sensitive paralytic strains contain mutations in genes that encode ion channels, components of the synaptic machinery, and other proteins required for generating and transmitting electrical signals in the nervous system. (LOUGHNEY et al. 1989; ATKINSON et al. 1991; PALLANCK et al. 1995; TITUS et al. 1997; LITTLETON et al. 1998).

Neurodegeneration mutants identified in the method of the invention are valuable research tools for identifying key proteins and biochemical pathways required for maintenance of neuronal viability. The mutants are also advantageously used to develop novel therapies for avoiding natural senescence and for treating and preventing neurodegenerative disorders in human and non-human animals.

In a working embodiment of the method, mutants were identified at a frequency that compares favorably with a prior large-scale screen of reduced lifespan flies, supra. In the selection step, temperature-sensitive paralytic mutants were identified at a frequency of 0. 1–0.2%. In the screening step, extensive neurodegeneration was observed in about 20% of the lines examined (0.02–0.04% of the mutagenized lines). The approach disclosed herein is preferred over prior methods for isolating neurodegeneration mutants, however, because it is much easier to score paralysis than lifespan and because reduced lifespan is not a characteristic of all mutants subject to age-related neurodegeneration.

Among the neurodegeneration mutants identified in the method are several novel dominant and recessive conditional temperature-sensitive and bang-sensitive paralytic mutations in *Drosophila* ATPalpha, having characteristic age-dependent behavioral abnormalities that can include conditional paralysis and a profound bursting physiological hyperexcitability defect. "Bursting" is described in Kasbekar, D. P. et al, "*enhancer of seizure*: A New Genetic Locus in *Drosophila melanogaster* Defined by Interactions with Temperature-Sensitive Paralytic Mutations," *Genetics* 116:423–431 (1987), incorporated by reference herein as if set forth in its entirety. Additionally, flies containing dominant ATPalpha mutant alleles exhibit a characteristic massive, age-dependent neurodegeneration. Maintenance of neuronal viability depends on normal sodium pump activity; aberrant ATPalpha function results in seizures and marked spongiform neuropathology.

In particular, the invention relates in part to a novel ATPalpha polypeptide having an amino acid sequence as disclosed in Genbank Accession No. XP-081160 modified relative to that sequence so as to have a substitution mutation affecting residue 981, residue 982, or both residues. Also, the invention relates to a polynucleotide that encodes any of the polypeptides of the invention. A polynucleotide of the invention can be provided on a cloning vector or expression vector. In the latter case, the vector can also comprise an upstream heterologous promoter and any other transcription or translation element advantageously employed in vivo or in vitro to obtain a polypeptide of the invention.

Other objects, features and advantages of the present invention will become apparent upon consideration of the following detailed description of the invention.

BRIEF DESCRIPTION OF THE SEVERAL VIEWS OF THE DRAWINGS

Not applicable.

DETAILED DESCRIPTION OF THE INVENTION

Neurodegeneration is enriched among various mutants characterized as having aberrant behaviors likely to be associated with altered or impaired neural function, namely temperature-sensitive paralytic mutants and bang-sensitive mutants. Numerous genes that encode ion channels and proteins required for synaptic transmission have been identified in temperature-sensitive paralytic mutants. In a method according to the invention, temperature-sensitive paralytic mutants or bang-sensitive mutants, or combinations thereof, are subjected to a histological screen, as described elsewhere herein, and those strains of mutant *Drosophila* exhibiting neurodegeneration on histological examination are selected for detailed phenotypic and molecular characterization or for use is subsequent methods for screening putative neuroprotective agents. The method provides an efficient means for targeted identification and collection of neurodegeneration mutants.

Those skilled in the art are familiar with methods for obtaining temperature-sensitive paralytic mutant flies strains, which can be isolated de novo according, e.g., to the method of Wu, C. F., et al., "A *Drosophila* mutant with a temperature-sensitive block in nerve conduction," *P.N.A.S. USA* 75:4047–4051 (1978), incorporated herein by reference as if set forth in its entirety. An adult or larval mutant is a "temperature-sensitive paralytic mutant" if it becomes paralyzed, ataxic or severely uncoordinated in less than 10 minutes when exposed to temperatures above 28° C. The behavioral phenotypes are reversible and the flies or larvae recover normal or nearly normal locomotor activity with a time course that varies from a few seconds to several hours depending upon the strain. One can decide whether a mutant is paralyzed, ataxic or severely uncoordinated by direct observation or by scoring performance on any one or, preferably more than one, of the running, climbing and flying tests described below in the Examples. A suitable strain that can function as a wild type control that does not become paralyzed at 37–38° C. is the Canton-S strain.

Those skilled in the art are familiar with methods for obtaining bang-sensitive paralytic mutant flies strains, which can be isolated de novo according, e.g., to the method of Grigliatti, T. A. et al., Molec. Gen. Genet. 120, 107–114 (1973), incorporated herein by reference as if set forth in its entirety. A mutant is a "bang-sensitive paralytic mutant" if it becomes paralyzed, ataxic or severely uncoordinated in less than 10 minutes when subjected to mechanical stress. Sufficient mechanical stress is provided, for example, by a vortex at highest speed for 10–20 seconds. The utility of the method does not depend upon the commercial availability of the starting mutants, but rather the use of same without regard to the means by which the strains are obtained.

In the method, the temperature-sensitive paralytic mutants or the bang-sensitive mutants, or both, are aged to an age at which neurodegeneration can be assessed. It is convenient, but not essential, to evaluate the mutant strains for neurodegeneration in the method at the midpoint age of the strain's survival curve which can be determined as described below. Neurodegeneration in the intact fly cannot be observed by the naked eye, but can be assessed by known histological methods, as detailed below, or by other diagnostic methods.

For a more thorough assessment of the neurodegeneration mutants revealed in the screen, the mutants can be compared to wild type flies in behavioral assays or electrophysiological techniques such as those performed at the larval neuromuscular junction, electroretinogram (ERGs), or those performed on adult flight muscles (Wu and Ganetzky, 1992). Synaptic transmission in the visual pathway can be measured by electroretinogram (ERG), an extracellular recording from the compound eye, that measures light-induced depolarization of photoreceptors as well as the synaptic-mediated responses of second-order neurons in the visual system (Hotta and Benzer, 1969; Pak et al., 1969). The ERG includes a component maintained during the entire light flash that corresponds to the light-dependent depolarization of the photoreceptor cells as well as on- and off-transients that appear at the beginning and end of a light flash respectively. The on- and off-transients represent responses from the second-order neurons in the lamina. If synaptic transmission between photoreceptor cells and laminar neurons is blocked, the on- and off-transients are preferentially lost.

The present invention also relates to various temperature-sensitive paralytic and bang-sensitive paralytic *Drosophila* mutants, preferably single point mutants, for which one inventive aspect is the recognition that the mutants exhibit substantial neurodegeneration as disclosed herein.

Additionally, the mutants identified in the method are advantageously used as targets for screening putative therapeutic agents for reversing the neurodegeneration associated with the mutants. In such methods, the mutant flies are exposed to a neuroprotecting amount of a putative neuroprotective agent. Neurodegeneration is assessed at or after the time at which neurodegeneration would be observed in flies untreated with the putative neuroprotective agent. The skilled artisan can readily perform the preparatory trials underlying the method to determine, for each strain tested, the amount of the agent to use, the duration of exposure to the agent, and the time at which neurodegeneration or neuroprotection should be assessed. The agent can be tested by direct injection into fly hemolymph using known methods. For example, using a pulled glass needle and a small volume injection apparatus such as the Drummond Nanoject (cat. no. 3-00-302-x) or related apparatus, a compound can be injected into the abdomen in a phosphate buffered saline. The procedure can be done without affecting the lifespans of the flies. It will also be appreciated by the skilled artisan that the screening need not be performed in flies, but can be performed in other animal systems in which neurodegeneration can be assessed.

The methods and mutants disclosed herein also find application in the field of identifying polynucleotide sequences in *Drosophila* that are associated with neurodegeneration and which have homologous sequences in vertebrate animals, especially mammals, and particularly in humans. Sequences in such animals identified as being associated with neurodegeneration can be isolated and introduced by transgenic methods into *Drosophila* or other model organisms, whereby the ability to employ neuroprotective agents to alter neurodegenerative outcomes can be assessed.

The invention will be more fully understood upon consideration of the following non-limiting Examples.

EXAMPLES

Example 1

In the selection step of the method of the invention, a set of mutant *Drosophila* strains were selected for a reversible, temperature-sensitive paralytic behavioral phenotype. The mutants primarily comprise independent, chemically induced, temperature-sensitive (TS) paralytic mutations. The mutants were isolated primarily in standard screens of the major chromosomes following mutagenesis with ethylmethane sulfonate (EMS). Flies were cultured on standard cornmeal, molasses agar medium at room temperature (21–23° C.). Flies and larvae were placed at 37–38° C. and flies or larvae that became paralyzed, ataxic, or severely uncoordinated in less than five minutes at the elevated temperature were retained for further study. The flies and larvae recovered normal or nearly normal locomotor activity within a few seconds to several hours, depending on the mutant strain. Many of the mutations affect genes that encode ion channels, components of the synaptic machinery, and other proteins required for the proper generation and transmission of electrical signals in the nervous system (WU and GANETZKY 1992; LITTLETON et al. 1999).

In the screening step of the method, the selected set of mutant strains were screened for age-dependent neurodegeneration by histological analysis. Mutant and control strains were screened as larvae, as young adults, and at the midpoints of their respective adult lifespan curves. The lifespan curves were determined as follows. Flies were raised to adulthood at room temperature (20–25° C.) and newly eclosed flies were placed in vials at low density (10–20 flies per vial) and incubated at 28° C. Males and females were kept in separate vials. Flies were transferred daily into fresh vials to minimize deaths caused by microbial infection or becoming stuck in the medium. The number of surviving flies was recorded daily. Survival curves were generated by plotting the percent of surviving flies as a function of time (in days). Surviving flies were removed for histological analysis and flies that suffered incidental deaths were excluded from the calculation. Statistical analyses were performed using Student's t-Tests.

Larvae, young, and aged adult flies (wild type controls and mutants) were screened for central nervous system (CNS) neurodegeneration, as indicated by a loss of tissue or vacuolar appearance of neural tissue of the brain, ganglia or eye tissue. To accomplish the screen in young and aged flies, heads were removed and were fixed in freshly prepared Carnoy's fixative at room temperature for 4–12 hours and processed into paraffin using standard histological procedures. Heads were embedded to obtain sections. Serial, frontal 4 uM sections were obtained, stained with hematoxylin and eosin and examined under a light microscope (n>25, each genotype) for gross neuropathology. For ventral ganglia examination the bodies were fixed similar in Carnoy's and processed into paraffin using standard histological procedures. Serial, saggital 4 uM sections were obtained, stained with hematoxylin and eosin and examined under a light microscope (n>25, each genotype) for gross neuropathology. For larvae, the entire CNS was removed, fixed in Bouin's, and processed into JB-4 embedding medium (Polysciences). Horizontal, 3 uM sections were obtained and stained with hematoxylin and eosin and then examined under a microscope (n>12, each genotype).

Among approximately 80 different temperature-sensitive mutant lines examined, 10 exhibited extensive CNS neurodegeneration. Five additional mutants displayed significant, but less dramatic, neurodegeneration. Additionally 6 control strains were examined for frequency and types of pathology that appear in aged wild type animals. The high frequency of neurodegeneration mutants among this collection demonstrates the utility of this approach.

One mutant revealed in the screen, vacuous (vacu), incurred extensive neuropathology. vacu is a recessive mutation generated on an st-marked third chromosome that was originally identified on the basis of larval paralysis at 38° C. Mutant larvae placed on a heated agar slab immediately cease crawling; in contrast, wild type larvae crawl vigorously at 38° C. Paralysis of vacu larvae reverses rapidly upon return to permissive temperatures. The lifespan of vacu at 28° C. is only about half that of controls—both fifty percent and maximal age are reduced in vacu animals (19.3 and 41.5 days) versus wild type (43.6 and 50.7) ($p<0.001$). The reduced lifespan of vacu is characteristic of this mutant and is not a phenotype shared by all temperature-sensitive paralytic mutants.

Histological analysis of frontal sections of heads from vacu adults revealed readily observable neurodegeneration with widespread and massive loss of neural tissue in the neuropil of the central brain and in the optic lobes (evident as the appearance of apparent vacuolization throughout these regions). Neuropathology is highly-penetrant in aged vacu animals: every animal tested exhibited significant gross pathology (n>60 animals). In contrast, aged control animals never exhibited significant gross pathology and it was rare to observe even a single vacuolar clearing (n>50 animals). Similar neurodegeneration was also readily observed in sagittal sections of the thoracic ganglion of vacu adults. The thoracic ganglion pathology is also highly-penetrant in vacu animals.

vacu neurodegeneration is progressive and varies as a function of developmental stage and age. No obvious evidence of neurodegeneration was observed in the third instar larval CNS, even though vacu larvae showed a strong behavioral defect. Likewise, young vacu adults did not exhibit neurodegenerative phenotypes within 36 hours post-eclosion. The age-dependent decline in behavior that correlates with the onset of observable neuropathology is similar to what is seen in progressive neurodegenerative diseases in humans.

Behavioral defects in the vacu adult flies also become more apparent with increasing age. Four groups of flies, corresponding to "young" and "aged" populations of wild type and vacu flies, were tested in the behavioral assays. Ten samples of 20 flies each (n=200 for each group) were collected for each of these four groups. Young flies were collected within 24 hours of eclosion and aged for 24–48 hours at 28° C. before testing. Aged flies were also collected within 24 hours of eclosion and maintained at 28° C. for 11 days. Each sample of flies was subjected to the same set of behavioral assays in the same order to test running, climbing, and flight abilities.

In a first behavioral assay (running), flies were placed at one end of a darkened, horizontal tube and allowed to run toward a light source at the other end. Eight flies were randomly selected from each sample and placed in a 10 mL glass pipette, sealing both ends with wax film to prevent escape (n=80 animals per group). One end of the pipette (20 cm) was darkened by placing it inside a dark-colored foam block. With the pipette secured horizontally in the foam, light from a fiber optic lamp was shined directly into the exposed tip of the pipette. The lamp was placed as close to the tip of the pipette as possible. For each trial, the flies were knocked to the foam-covered end of the pipette then returned to the horizontal test position. The time required for the first six flies of each sample to enter the light-exposed portion of the pipette was measured in seconds. Four trials were completed for each sample. Each individual fly was given a score and these scores were then averaged for each sample for statistical analysis using Student's t-test.

Young wild type adults typically required less than 30 seconds (s) to run the length of the tube. Young vacu adults were somewhat slower than the controls, although they still ran the length of the tube in only about 45 s. Although newly eclosed vacu adults did not show any overt behavioral abnormalities other than generally sluggish locomotor activity, either at 20° C.–22° C. or at 37–38° C., as they age vacu adults differ markedly from wild type in viability and locomotor activity. While both wild type and vacu adults showed an age-dependent decrement in this assay (p<0.001), the decline was much more severe for vacu (7.5 versus 5.1 fold increase). Aged wild type adults ran the tube in about 150 s, whereas aged vacu adults required around 300 s. Aged wild type performed significantly better than vacu animals (p<0.001).

In a second behavioral assay (climbing), ten flies were randomly selected from each sample and placed in a 250 mL glass graduated cylinder, sealed at the top with wax film to prevent escape (n=100 animals per group). A fiber optic lamp illuminated the cylinder from the top. The flies were gently knocked to the bottom of the cylinder and flies climbed up a vertical tube against gravity toward the light source. The time required for 50% of the flies to cross a line 17.5 cm from the bottom of the tube was determined. Four trials were completed for each sample. Times for each sample were averaged for statistical analysis using Student's t test. Young wild type adults reached this point within 5–10s. Wild type flies showed a small age-dependent decrease in behavior (p<0.001), requiring about 30–35s to cross the line. In contrast, vacu adults, both young and old, performed very poorly in this assay. Neither group of vacu adults completed the task within the total five minute period allotted. Because even young vacu adults behaved so poorly in this assay, it was not possible to assess whether vertical climbing ability declined further with age.

In a third behavioral assay (flight), the assay was performed essentially as in Benzer (1973) and in Elkins et al. (1986). Flies were dropped into the top of a 500-mL glass graduated cylinder through a glass funnel whose end reached the 500-mL mark (n=200 per group). The inside surface of the cylinder was coated with paraffin oil causing flies to become stuck where they strike the wall. The strongest fliers initiate flight immediately and become stuck near the top of the cylinder. The weaker fliers fall farther and become stuck near the bottom of the cylinder. The vertical distribution of each group of flies over the length of the cylinder was determined to measure flying ability. These scores were then averaged for each group of flies for statistical analysis using Student's t-test.

Both wild type and vacu flies show an age-dependent decrease in flight ability but vacu flies of both age groups perform markedly worse than wild type and the decline in flight ability with age is more severe for vacu.

The larval paralytic phenotype of vacu was mapped to between st (3–44.0) and Sb (3-58.2) by recombination analysis. Among 80 recombinants recovered between st and Sb, 24 were between st and vacu, placing vacu approximately 4.3 map units to the right of st. The mapping was refined using existing deletions in the relevant interval to determine the cytological location of vacu. Df(3R)by10 (85D8-12; 85E7-F1), Df(3R)by62 (85D11-14; 85F6), and Df(3R)by77 (85D8-12; 86B4) all uncovered the vacu paralytic phenotype, whereas Df(3R)by416 (85D10-12; 85E1-2) did not. These results suggest that the vacu mutation is either in the 85D8-85D 10 interval or in the interval between 85E 1-3 and 85E7-F 1. No other deletions are currently available to resolve these two possibilities.

Anomalous electrical activity in the mutant suggests that loss of vacu function may result in neuronal hyperexcitability. Electroretinograms (ERGs) were recorded essentially as described (PAK et al. 1969; HOTTA and BENZER 1969). Briefly, flies were anesthetized with $CO_2$, their wings and anterior legs were surgically removed, the flies were immobilized in plasticine, and were allowed to recover for 15 minutes. A temperature-controlled stage was used with a temperature probe inserted into the plasticine adjacent to the animal. Glass recording and reference electrodes filled with 3M KCl were placed in the cornea and thorax, respectively. Following dark adaptation (5 minutes), photoreceptor responses to brief light exposures were recorded. Traces were amplified using an Axopatch 1-D amplifier in current clamp mode (clamping at zero) and recorded using Clampex 6.0.3 software (Axon Instruments). Current traces were filtered at 1 kHz and consecutive traces are reported from representative animals (n>6 for each genotype). Recordings were taken at temperatures between 20° C. and 37° C. in the following order: 20° C., 34° C., 37° C. and 22° C.

Sporadic depolarization events were observed at all temperatures in vacu animals. Bursts of apparent electrical activity are present at 34° C. and 37° C. in vacu animals but not in wild type animals. The ERGs of adult vacu flies appeared relatively normal both at 20° C. and at 37° C., despite the noted behavioral deficits. However, recurrent spikes are apparent in the ERG trace at 20° C. before, during, and after the light exposure. At 34° C.–37° C., more prominent sustained bursts of apparent activity are observed both preceding and following the light flash. Upon return to 20° C., the more extreme bursting activity disappears but the small recurrent spikes persist. We believe that this excessive activity originates in the ventral ganglion and is being detected by the ERG ground electrode, which is inserted into the thorax. Similar bursting activity has been previously observed in mutants such as seizure (sei), which are known to cause neuronal membrane hyperexcitability (ELKINS and GANETZKY 1990; TITUS et al. 1997) as well as in some bang-sensitive mutants, and such activity has been interpreted as neural hyperactivity and physiological seizures (PAVLIDIS and TANOUYE 1995; KUEBLER and TANOUYE 2000; KUEBLER et al. 2001). The massive degeneration seen in the optic system appears to be light-independent.

Accordingly, it is shown in this Example that a mutant selected on the basis of its temperature-sensitive paralytic phenotype was identified as a neurodegeneration mutant in accord with the method of the invention. Further, the neurodegeneration mutant was characterized by behavioral and synaptic transmission assays.

Example 2

In extensive screens for mutations that cause neuronal dysfunction in *Drosophila* we identified several dominant mutations in *Drosophila* were identified that result in behavioral abnormalities. Two mutants were independently isolated, temperature-sensitive (TS) paralytic mutations and a third was isolated as a bang-sensitive paralytic mutation. All three mutations are homozygous lethal early in development. In accord with the method of the invention, prior selection of temperature-sensitive paralytic mutants and/or bang-sensitive paralytic mutants sensitizes a subsequent screen for neurodegeneration mutants. Mutants DTS1 (ATPalpha$^{DTS1}$) and DTS2 (ATPalpha$^{DTS2}$), described below, exhibit neurodegeneration.

Fly stocks were maintained on standard cornmeal, molasses, agar media at 22–28° C. Wild type and control flies refer to Canton S, unless otherwise specified. The DTS1 mutation was obtained in an EMS mutagenesis of Canton S in a screen for dominant temperature-sensitive paralytic mutations. DTS2 was obtained in a similar manner, although cn,bw animals were mutagenized. Upon exposure to 37–38° C., DTS1/+ and DTS2/+ adults become completely paralyzed within 10–30 seconds except for minor twitching of the tarsi. Following a three-minute exposure to the restrictive temperature, the flies regain the ability to stand after one to two minutes at the permissive temperature (<30° C.) and require another several minutes before they begin to walk. Even without exposure to elevated temperatures, both DTS1/+ and DTS2/+ heterozygotes appear to be somewhat sluggish and do not walk or climb as rapidly as wild type flies. Homozygotes for DTS2 and DTS1 die early in development. Mutants DTS1 and DTS2 also manifest a novel temperature-dependent bang-sensitive phenotype. Assays of bang sensitivity and temperature sensitivity were performed as described (GANETZKY, 1982; WU, 1978). When stocks of these flies are maintained at 20–22° C. and tested at the same temperature, they show no obvious bang-sensitivity. However, when the stocks are maintained at 28° C., DTS2/+ and DTS1/+ flies are viable but show bang-sensitive paralysis lasting for 5–30 seconds when tested at room temperature, even when the flies are allowed to accommodate to the temperature shift for several hours. Revertants of DTS1 and DTS2, designated DTS1$^{R1}$, DTS1$^{R2}$, DTS2$^{R1}$, DTS2$^{R2}$ and DTS2$^{R3}$, were generated in a screen of gamma ray treated mutants that were no longer TS paralytic.

Mutant H64 was obtained from an ENU mutagenesis of a roe, pp stock. H64 was originally identified on the basis of its bang-sensitive phenotype, and appeared to be an autosomal dominant mutant. When maintained as heterozygotes over the TM6B balancer chromosome marked with Tb, no non-Tb larvae were observed, indicating that H64 homozygotes are lethal prior to the second larval instar. When tested for bang-sensitivity, H64/TM6 adults become completely paralyzed for 10–35 seconds. Upon recovery from paralysis, up to five minutes of additional time is required before these animals regain full activity. These mutants show no evidence of temperature-sensitive paralysis at 37–38° C. but even at 20–22° C. when not subjected to mechanical stimulation, they are often sluggish and spend most of their time on the bottom of the vial.

Complementation tests for recessive lethality among H64, DTS1, and DTS2, in all pairwise combinations (Table 1) shows that all three mutants fail to complement one another, suggesting that they all share lethal mutations of the same gene. The conditional paralytic phenotype of DTS1, DTS2 and H64 was mapped relative to Gl, Sb, H by recombination. All three mutations mapped in the same approximate chromosome location (70.5, 70.3 and 69.5 cM, respectively) and were tightly linked to H. This map position corresponds to the 92D–93B cytological region, which is in the chromosomal region of ATPalpha.

TABLE 1

Viability of existing ATPalpha alleles with the new conditional mutants and their revertants.

|  | DTS1 | DTS1$^{R1}$ | DTS1$^{R2}$ | DTS2 | DTS2$^{R1}$ | DTS2$^{R2}$ | DTS2$^{R3}$ | H64 |
|---|---|---|---|---|---|---|---|---|
| ATPalpha$^+$ | TS, BS$^{td}$ | BS | BS | TS, BS$^{td}$ | BS | mTS, BS | BS | BS |
| DTS1 | 1 | 1 | 1 | 1 | 1 | 1 | 1 | 1 |
| DTS1$^{R1}$ | 1 | 1 | 1 | 1 | 1 | 1 | 1 | 1 |
| DTS1$^{R2}$ | 1 | 1 | 1 | 1 | 1 | 1 | 1 | 1 |
| DTS2 | sl, TS | 1 | 1 | 1 | 1 | 1 | 1 | 1 |
| DTS2$^{R1}$ | 1 | 1 | 1 | 1 | 1 | 1 | 1 | 1 |
| DTS2$^{R2}$ | 1 | 1 | 1 | 1 | 1 | 1 | 1 | 1 |
| DTS2$^{R3}$ | 1 | 1 | 1 | 1 | 1 | 1 | 1 | 1 |
| H64 | 1 | 1 | 1 | 1 | 1 | 1 | 1 | 1 |
| ATPalpha$^{2206}$ | BS, TS | 1 | 1 | dl | 1 | 1 | 1 | 1 |
| ATPAlpha$^{01453}$ | sl, TS | 1 | 1 | 1 | 1 | 1 | 1 | 1 |

TS = temperature-sensitive paralysis (38 C.),
BS = bang-sensitive paralysis;
BS$^{td}$ = temperature-dependent bang-sensitive paralysis (28 C.);
mTS = modified TS;
l = early developmental lethal;
sl = semi-lethal (5% versus expected 25%);
dl = lethal during pupariation and eclosion.
Note:
ATPAlpha$^{2206}$/ATPAlpha$^{01453}$ flies are not bang-sensitive but have reduced viability (10% versus expected 50% of offspring).

DTS1 and DTS2 mutants display a marked age-dependent decrement in locomotor activity. In comparison with age-matched wild-type flies, the mutants become quite sedentary with a premature loss of both walking activity and flight ability.

DTS1 and, to a lesser extent, DTS2 and ATPalpha$^{2206}$ were determined to be short-lived, whereas H64 has an essentially normal lifespan. Comparisons of the age of 50% survivorship for each genotype demonstrate a significant reduction in lifespan for DTS1, DTS2 and ATPalpha$^{2206}$ relative to wild type. The time required to reach 50% survivorship for each population was used to compare the lifespans of ATPalpha mutants with control strains TM6, Ubx/+, TM6, Tb/+, and Canton S. Lifespan is significantly reduced in ATPalpha$^{DTS1}$, ATPalpha$^{DTS2}$ animals (17 and 27 days) and moderately reduced in ATPalpha$^{2206}$ (36 days) versus controls (41–45 days) ($p<0.001$, all comparisons to Canton S). In contrast, the lifespan of ATPalpha$^{H64}$/+ flies did not differ significantly from Canton S ($>0.5$).

The reduced lifespan and premature motor activity loss exhibited by both dominant mutants are consistent with the phenotypes of other Drosophila neurodegeneration mutants. To investigate the possibility that these mutants also experienced neurodegeneration, we performed a histological analysis of DTS1/+, and DTS2/+. Wild-type and mutant adults were aged to approximately 50% survival on their respective lifespan curves and histological examination was performed, as in Example 1. Serial frontal sections revealed extensive neuropathology in the brains of all ATPalpha mutants. In DTS2/+ and DTS1/+ animals, vacuolar structures were distributed widely throughout the central brain and optic regions. This phenotype was never observed in wild-type animals which only rarely contained small vacuolar structures. Also, many DTS2/+ and DTS1/+ animals showed a highly-localized region in the ventral lateral region of the central brain with increased pathology resulting in large holes in these regions.

Neurodegeneration was also observed in H64 and ATPalpha$^{2206}$, which are both recessive loss-of-function ATPalpha alleles. In contrast to that seen in the dominant ATPalpha alleles, the neurodegeneration was less severe, especially in ATPalpha$^{2206}$, and appeared as sporadically localized vacuolar pathology throughout the brain. In contrast to the massive degeneration seen in DTS1 and DTS2, sei$^{TS2}$, another conditional mutant with a profound bursting physiological defect, showed only sporadic large vacuolar structures that were uncommon in age-matched control animals. Histological examination of each genotype (n>50, each genotype) demonstrated that the penetrance of the neuropathology observed in DTS1 and DTS2 was close to 100% and the distinctive patterns of neurodegeneration were reproducible for each mutant.

As is the case with many human neurodegenerative conditions, neurodegeneration in these mutant animals appears to be age-dependent and not the result of developmental defects. Young individuals of the ATPalpha mutants revealed little or no evidence of neurodegeneration in the brain or in sagittal sections of the thoracic ganglion, which were also examined for pathology in young and aged animals. In accord with the results found in the brain, the thoracic CNS also undergoes age-dependent neurodegeneration in DTS1 and DTS2 mutants.

To refine the cytological location of the mutants, we took advantage of the fact that DTS1 and DTS2 behave as dominant gain-of-function mutations and therefore should be revertible by second-site mutations within the gene that completely eliminate its function. Therefore, we screened for gamma ray-induced revertants of DTS1 and DTS2 that were not paralyzed at the restrictive temperature. Two revertants of DTS1 (DTS$^{R1-R2}$) and three revertants of DTS2 (DTS2$^{R1-R3}$) were recovered. DTS1$^{R2}$, DTS2$^{R1}$, and DTS2$^{R2}$ were all associated with cytologically visible breakpoints in the 93A5-93B1,2 interval that disrupted ATPalpha and would be expected to abolish its activity.

The remaining two revertants, DTS1$^{R1}$ and DTS2$^{R3}$, were not associated with gross physical disruption of the ATPalpha gene by cytological or PCR analysis. However, direct sequence analysis of genomic DNA revealed that DTS1$^{R1}$ is associated with a 4 bp deletion (ATPalpha deletion 2713-16) that results in a frameshift mutation in the ATPalpha coding region that is predicted to cause premature truncation of the protein product resulting in ATPalpha deletion 905-C, if any protein is actually made. Sequence analysis of DTS2$^{R3}$ revealed two point mutations resulting in a predicted ATPalpha protein having E to A (39) and L to F (346) substitutions. Accordingly, all five DTS1 and DTS2 revertants have molecular defects in the ATPalpha gene consistent with loss-of-function mutations that can revert dominant TS mutations.

Each revertant contained a lesion in ATPalpha, confirming that the original DTS1 and DTS2 mutations, and by inference H64, are ATPalpha alleles. Each revertant contains mutations consistent with loss-of-function mutations and all but DTS2$^{R2}$ appear to be null alleles of ATPalpha. We found no significant phenotypic differences among the five revertants and H64, suggesting that the H64 mutation may be a loss-of-function allele and that phenotypes arose in H64 and the revertants due to haploinsufficiency of ATPalpha. These data are consistent with the observation that a large deficiency, Df(3R)r-1G6/TM3, that removes ATPalpha causes a bang-sensitive phenotype (LEBOVITZ, 1989).

Molecular characterization of the revertants provided a strong indication that the original dominant mutations also resided in ATPalpha. We identified the original lesions associated with these mutants by direct sequence analysis of genomic DNA. Both ATPalpha$^{DTS1}$ and ATPalpha$^{DTS2}$ mutations cause predicted single amino acid substitutions in the C-terminus of the protein. This analysis revealed a single basepair change (G to A) in DTS2 which is predicted to cause a D to N substitution at position 981. DTS1 is also associated with a single basepair change (G to A) that results in an apparent E to K substitution of the next residue, at position 982. Both of these residues are conserved in ATPalpha proteins from representative species throughout the animal kingdom: Hs (Homo sapiens), Rn (Rattus norvegicus), Gg (Gallus gallus), Dr (Danio rerio), Ee (Electrophorus electricus), Dm (Drosophila melanogaster), Cf (Ctenocephalides felis, cat flea), As (Artemia franciscana, brine shrimp), Ce (Caenorhabditis elegans), Hv (Hydra vulgaris, hydra). The skilled artisan understands the degenerate three nucleotide codon system for encoding amino acids, and, being put in possession of the amino acid sequence of these mutations, is fully able to deduce numerous polynucleotides capable of encoding the mutant ATPalpha proteins of the invention.

It is extremely unlikely that these changes simply represent silent polymorphisms because they fall within a segment of the protein that is very highly conserved overall and the affected residues in particular are completely invariant in Na$^{+/K+}$ ATPase alpha subunit proteins from hydra to human. In fact, these amino acid residues are even conserved in the more distantly related H$^+$/K$^+$ ATPase alpha subunit proteins. As expected, these substitutions are still present in the corresponding revertants, but are not found in any other control chromosome that we sequenced. It is striking that different alleles of the same gene, particularly two mutations affecting adjacent amino acids, could have such similarities in the patterns of neurodegeneration with different times of onset. These mutations may therefore identify key residues that serve important regulatory roles.

Prior proteolysis and chemical cross-linking experiments on $Na^{+/K+}$ ATPase proteins have demonstrated that the C-terminus (M8-M10 region) of this protein makes intra-subunit contacts with the M1-M2 region as well as inter-subunit contacts with the beta subunit. Without intending to be limited to a scientific theory underlying the invention, the dominant ATPalpha mutations of the invention could perturb one or both of these interactions, affecting regulation of the protein and resulting in gain-of-function phenotypes. Scanning mutagenesis of oxygen-containing residues predicted to be cytosolic or at the membrane/cytosol interface has been performed (Arguello (1999). As such, one of the residues in which we identified a lesion, D#981 (D995 in sheep $Na^{+/K+}$ ATPase alphal isoform), has already been the subject of investigation. Those investigations demonstrate that the D995A mutations do not affect cation-enzyme interaction but do appear to impair protein maturation. The dominant phenotypes we observed in ATPalpha$^{DTS1}$ and ATPalpha$^{DTS2}$, which are more severe than those caused by null mutations of the same gene, suggest that these mutations cause a gain-of-function or have a dominant negative effect. Until recently it was thought that an alpha-beta protomer, the minimal unit of the enzyme required for function in vitro, was also the in vivo functional unit, making it more difficult to account for a dominant-negative effect. However, more recent data indicate that the protein may exist as a tetramer in vivo (Taniguchi, 2001). If the presence of even one mutant subunit could affect the activity or processing of the oligomeric complex, a dominant-negative effect could be readily explained.

The effect of these mutations was further verified by generating RT-PCR products from the ATPalpha mRNA isolated from DTS1, DTS2, H64 mutants and all of the revertants and then digesting these products with appropriate restriction enzymes to distinguish whether the RT-PCR products were derived from RNA transcribed off of mutant or wild-type alleles. In each case, the data demonstrated that the mutant chromosomes bearing the primary DTS1, DTS2 and H64 mutations still produced ATPalpha transcripts; however, there was no detectable expression of an ATPalpha transcript from the homolog containing DTS1$^{R2}$, DTS2$^{R1}$ and DTS2$^{R2}$.

Without intending to be limited to any particular scientific theory underlying this aspect of the invention, the specific mutant residues identified in ATPalpha$^{DTS1}$ and ATPalpha$^{DTS2}$ may further destabilize ATPalpha protein resulting in some thermal unfolding at temperatures that are permissive for wild type ATPalpha. Scanning calorimetry studies of wild type pig kidney $Na^{+/K+}$ ATPases have uncovered three domains of thermal unfolding, one mapping to the beta subunit and two to the alpha subunit (GRINBERG, 2001).

A profound temperature-dependent neuronal bursting electrophysiological phenotype was also noted in the DTS1 and DTS2 dominant mutants. Extracellular thoracic recordings (ETRs) were recorded essentially as described for electroretinograms, supra. Unevoked depolarization events (also referred to herein as hyperexcitability and bursting physiology) were seen predominately at elevated temperatures in ATPalpha and seizure mutant animals but do not appear in wild type. The bursting activity was apparently recorded extracellularly by the electrode positioned in the thorax just beneath the flight muscles and likely represents electrical activity in the dorsal longitudinal flight muscles in response to neuronal hyperexcitability in the flight motor pathway. This interpretation is supported by the observation of a similar, but somewhat more severe phenotype, for sei$^{ts2}$, a $K^+$ channel mutation known to cause neuronal hyperexcitability (Elkins, 1990; Titus, 1997). The bursting activity seen in DTS2 and DTS1 is consistent with defects in the sodium pump, which could result in more depolarized membrane resting potentials.

The physiological defect is present in very young adults, prior to the occurrence of any overt neurodegeneration. This result supports the conclusion that neural dysfunction, manifest as hyperexcitability, might lead to neuropathology. However, sei$^{ts2}$, a mutation in the gene encoding ERG-type $K^+$ channels, which also causes extensive bursting activity, is not associated with the kind of extensive neurodegeneration seen in ATPase alpha subunit mutants. These data suggest that hyperexcitability alone is not sufficient to cause neurodegeneration.

The physiological bursting phenotypes such as those seen in sei$^{ts2}$ and reported here for dominant ATPalpha mutants have been observed in other Drosophila behavioral mutants. Such mutants are being used to investigate the physiological basis for seizure disorders such as epilepsy (KUEBLER, 2001). Our results demonstrate that ATPalpha is another gene that can cause physiological seizures when mutated in particular ways. The dominant ATPalpha mutants in Drosophila should provide a very useful experimental model for investigating physiological seizures, neurodegeneration, and the connection between them.

Example 3

Exon Analysis

The genomic locus of ATPalpha contains previously undescribed exons. Using primers directed towards exons 4 and 9 for RT-PCR reactions, we identified four exons that appeared to be mutually exclusive and named them 6a, 6b (formerly exon 6, NCBI database), 6c (formerly 13), and 6d. To date, all Drosophila ATPalpha cDNAs examined contained the exon corresponding to 6b (LEBOVITZ, 1989; SUN, 1998; Sun, 2001). Here, each of 123 ATPalpha clones contained one and only one member from the set of exons 6a, 6b, 6c, and 6d, indicating that these exons are utilized as mutually exclusive alternative cassettes. All four alternative exons are identical in length (94 bp). All of the newly described exons, as well as those previously known, appear to have wild type coding potential with the exception of the mutations discovered to affect residues 981 and 982, as described elsewhere herein. The sequences of new genomic exons 6a–6d are presented in the Sequence Listing as SEQ ID NO:2, 4, 6, and 8, respectively. The predicted amino acids encoded by genomic exons 6a–6d are presented as SEQ ID NO:3, 5, 7 and 9, respectively.

To clarify the exon 6 region, standard RT reactions were performed with a gene-specific primer directed to exon 9 (TTAATAGTAGGTCTCCTGCTCC-OH, SEQ ID NO:10), M-MLV Reverse Transcriptase (Promega) and 10 micrograms whole RNA isolated from embryos or adults using a modified LiCl/Urea preparation (AUFFRAY, 1980). Standard PCR reactions were performed as follows with primers directed toward exons 4 (TCAACACCGACGACAT-CAACTTCC-OH; SEQ ID NO:11) and 9 (GGTTGCG-GCGCAAGTAGAAACGACG-OH, SEQ ID NO:12): 94° C. denaturing (45 seconds); 57° C. annealing (45 seconds);

and 72° C. extension (2 minute), for 40 cycles. Products were cloned using the TOPO T/A Cloning Kit and One Shot *E. coli* (Invitrogen). Mini-plasmid preparations of transformants were analyzed by restriction digestion to determine which exon 6 was present. DraIII/EcoRI (NEB) double digests were diagnostic for exon 6b, and BsmBI (NEB) and BstYI (NEB) were diagnostic for exon 6c and 6d, respectively. Clones assayed negative for 6b,c and d were sequenced to verify that they contained exon 6a.

The alternative exons 6 encode part of the M6 transmembrane segment and the entire M6-M7 intracellular domain of the ATPalpha protein. Evolutionary comparisons show that this region is highly-conserved between worms and humans and that all three alternative exons encode most of these conserved residues. However, the three isoforms exhibit intriguing variations as well. In comparison with $Na^{+/K+}$ ATPase alpha proteins of other species, exon 6c is most similar to the corresponding region of the nematode protein encoded by eat-6, and to the sequence encoded by the vertebrate orthologs. Several residues that vary among vertebrate $Na^{+/K+}$ ATPase alpha paralogs and between $H^{+/K+}$ ATPase alpha sequences vary among exons 6a, b, c, and d. These data suggest that *Drosophila* generates functionally diverse and structurally diverse ATPalpha proteins through alternative exon 6 splicing. Because the *Drosophila* genome contains one known $Na^+/K^+$ ATPase structural gene and one predicted paralog with good sequence homology (CG17923) rather than four, as appear to exist in most vertebrates, alternative splicing may be a mechanism for generating diversity in *Drosophila* comparable to that made available in vertebrates by the existence of several genes.

The cassette encoded by exons 6 extends from I/V797 to R827 (corresponding with V814 to R845 of sheep $Na^{+/K+}$ ATPase alpha subunit), which encompasses the entire predicted cytosolic loop between M6 and M7 and part of the M6 transmembrane domain. Previous data have demonstrated that the M5-M6 region functions in cation binding and ion transport. Specifically, in mammals S775, Y771, E779, and F786 have been implicated in $K^+$ coordination, $Na^+$ interactions, voltage-dependence, and ouabain binding, respectively. In addition, D804 and D808, located in M6, are reported to be cation-coordinating residues. ADP binding has been shown to protect the M6-M7 cytoplasmic loop against tryptic digestion (LUTSENKO, 1994). The segment including YTLTSNIPEI (SEQ ID NO:13) in the fifth transmembrane segment is especially important in determining ion selectivity of the pump (PEDERSON et al, 1998). Together, these and other data demonstrate the central importance of the M5-M6 region to ATPase alpha function. The existence of multiple, alternatively spliced versions of exon 6 in the *Drosophila* ATPalpha gene suggest that the sequence differences encoded by these alternative exons could have profound functional consequences on pump kinetics, ion selectivity, or regulatory properties. Previous functional studies of ATPalpha in *Drosophila* have all utilized cDNAs that contained the same exon 6 splice variant (exon 6b). The discovery of multiple exons that generate additional structural diversity for this important region of the protein may reveal previously unsuspected functional diversity as well.

Example 4

Alternative 5' End Splicing

In addition to alternative splicing in exon 6, ATPalpha also exhibits extensive alternative splicing at its 5' end. Semi-quantitative RT-PCR and analysis of many isolated clones suggests that transcripts initiating near exon 12 are more abundant and diverse than those generated from exon 0. Semi-quantitative RT-PCR was performed on adult whole RNA as published, with some minor modifications (Palladino et al., 2000b). Primers directed to exon 0 and 12 sequences were separately used in combination with a reverse primer directed toward exon 3. RP49 primers directed to a gene for ribosomal protein were added to the reaction as a control at cycle 5. Samples were taken every other cycle from 16 and 28 and resolved on an agarose gel stained with ethidium bromide.

Quantification of gel fluorescence was performed on cycle 20 products using NIH image software. The RT-PCR products were cloned, as above, and representatives of each size clone were directly sequenced to document the splicing events. Exon 12 products became evident approximately 4 PCR cycles before those from exon 0, suggesting these transcripts are approximately 12–16 fold more abundant in adults. Consistent with this interpretation, fluorescence quantification revealed the ratio of ATPalpha products to RP49 product was 5.6±1.1 and 0.4±0.07 for exon 12 and exon 0 products, respectively (Error is SEM). Also, whereas an exon 0-directed upstream primer produces only one visible RT-PCR product (334 bp), at least four distinct products are evident when the upstream primer is directed toward exon 12 sequences, the most abundant of which are 577 bp and 349 bp.

Analysis of isolated clones is consistent with these interpretations and identifies the most abundant products from exon 12, as well as rare splice products. These analyses have identified a new multi-exon, 14/15, and a potentially new translational start in exon 15. These data suggest that three alternate N-termini exist for this protein; two long forms with putative translational initiation sites in exon 0 and 15 (amino acid sequences are provided as SEQ ID NO:14 and SEQ ID NO:15, respectively), and a short form with an initiation site in constitutive exon 2 (amino acid sequence is provided as SEQ ID NO:1). The same neurodegeneration mutations on SEQ ID NO:14 that correspond to mutations at residues 981 and 982 on SEQ ID NO:1 are at residues 1020 and 1021 of SEQ ID NO:14, respectively; the same neurodegeneration mutations on SEQ ID NO:15 that correspond to mutations at residues 981 and 982 on SEQ ID NO:1 are at residues 1016 and 1017 of SEQ ID NO:14, respectively.

In summary, Examples 2, 3 and 4 demonstrate again that temperature-sensitive and bang-sensitive mutants are an advantageous pool from which to screen for neurodegeneration mutants. In these embodiments, the neurodegeneration mutants were further characterized at the molecular level. These data establish *Drosophila* as an important model that can be used to better understand important human disease conditions associated with the affected gene and its biochemical pathways, and, by extension, for other conditions associated with other genes identified in the selecting and screening method of the invention. The molecular analysis of ATPalpha promoter usage and alternative splicing complements the mutant analysis and helps to further develop this important model.

Example 5

We have described in previous examples Na/K ATPase alpha subunit (ATPalpha) alleles and vacu mutants that manifest a neurodegenerative phenotype. All of these alleles, and in fact any allele with a loss of function mutation in the ATPase alpha subunit, can be used for evaluating the neuroprotective agent. In addition to the ATPalpha alleles, we have similarly identified other neurodegenerative alleles that can be used for evaluating neuroprotective agents.

One of these alleles we identified, has a lesion in a gene known as CG4684, the sequence of which is provided as SEQ ID NO:16. The lesion results in a P866Q in an allele known as 565. The wild type (SEQ ID NO:16) and the lesion (P866Q) proteins are within the scope of the present invention. In addition, polynucleotides that encode the above proteins are also within the scope of the present invention. This allele can be used in the method of the present invention for evaluating neuroprotective agents.

Littleton et al, *Proc Natl Acad Sci USA* 88 (21): 12233–12238 (2001), which is herein incorporated by reference in its entirety, disclosed several NSF1 alleles: TP7 (P398S), ST53 (S483L), ST17 (G274E) and G4 (VQQ525-527GS). The amino acid sequence of the NSF1 protein can be found with NCBI accession number P46461 (provided as SEQ ID NO:17). We have found that these alleles manifest a neurodegenerative phenotype and thus can be used in the method of the present invention for evaluating neuroprotective agents.

*Mol Gen Genet* 256 (6): 602–610 (1997), which is herein incorporated by reference in its entirety, disclosed alleles with lesions on a voltage-dependent sodium channel (paralytic or para) with two lesions specifically identified: TS1 (I265N), DTS2 (A1506V), DTS3, ST109, TS 115. The amino acid sequence of the protein can be found with Swiss Protein accession number P35500 (provided as SEQ ID NO:18). We have found that these alleles manifest a neurodegenerative phenotype and thus can be used in the method of the present invention for evaluating neuroprotective agents.

*Science* 283 (5406): 1343–1345 (1999), which is herein incorporated by reference in its entirety, disclosed several axotactin alleles: 52, 8D and 6. They are all loss-of function alleles with non-specified disruptions in the axo gene. We have found that these alleles manifest a neurodegenerative phenotype. Thus these alleles and any other alleles that carry loss-of-function lesions on axotactin can be used in the method of the present invention for evaluating neuroprotective agents. Axotactin amino acid sequence is provided as SEQ ID NO:19. Partial axotactin amino acid sequence can be found with accession Fban0018296.

In *J Biol Chem* 274 (31): 22109–22113 (1999), which is herein incorporated by reference in its entirety, a Shab allele was disclosed: Shab$^1$ (R435Q). The amino acid sequence of the protein can be found with Swiss Protein accession number P17970 (provided as SEQ ID NO:20). We have found that the allele manifests a neurodegenerative phenotype and thus can be used in the method of the present invention for evaluating neuroprotective agents.

REFERENCES CITED

Arguello, J. M., Whitis, J., Cheung, M. C., and Lingrel, J. B. (1999a). Functional role of oxygen-containing residues in the fifth transmembrane segment of the Na,K-ATPase alpha subunit, Arch Biochem Biophys 364, 254–63.

Arguello, J. M., Whitis, J., and Lingrel, J. B. (1999b). Alanine scanning mutagenesis of oxygen-containing amino acids in the transmembrane region of the Na,K-ATPase, Arch Biochem Biophys 367, 341–7.

Asano, S., Io, T., Kimura, T., Sakamoto, S., and Takeguchi, N. (2001). Alanine-scanning mutagenesis of the sixth transmembrane segment of gastric H+,K+-ATPase alpha-subunit, J Biol Chem 276, 31265–73.

Atkinson, N. S., G. A. Robertson and B. Ganetsky, 1991 A component of calcium-activated potassium channels encoded by the *Drosophila* slo locus. Science 253: 551–555.

Auffray, C., and Rougeon, F. (1980). Purification of mouse immunoglobulin heavy-chain messenger RNAs from total myeloma tumor RNA, Eur J Biochem 107, 303–14.

Beal, M. F., Hyman, B. T., and Koroshetz, W. (1993). Do defects in mitochondrial energy metabolism underlie the pathology of neurodegenerative diseases?, Trends Neurosci 16, 125–31

Beguin, P., Hasler, U., Beggah, A., Horisberger, J. D., and Geering, K. (1998). Membrane integration of Na,K-ATPase alpha-subunits and beta-subunit assembly, J Biol Chem 273, 24921–31.

Benzer, S., 1973 Genetic dissection of behavior. Sci Am 229: 24–37.

Bignami, A., Palladini, G., and Venturini, G. (1966). Effect of cardiazol on sodium-potassium-activated adenosine triphosphatase of the rat brain in vivo, Brain Res 1, 413–4.

Blanco, G., and Mercer, R. W. (1998). Isozymes of the Na-K-ATPase: heterogeneity in structure, diversity in function, Am J Physiol 275, F633–50.

Buchanan, R. L., and S. Benzer, 1993 Defective glia in the *Drosophila* brain degeneration mutant drop-dead. Neuron 10: 839–850.

Calandriello, L., Curini, R., Pennisi, E. M., and Palladini, G. (1995). Spongy state (status spongiosus) and inhibition of Na,K-ATPase: a pathogenetic theory, Med Hypotheses 44, 173–8.

Coombe, P. E., and M. Heisenberg, 1986 The structural brain mutant Vacuolar medulla of *Drosophila* melanogaster with specific behavioral defects and cell degeneration in the adult. J Neurogenet 3: 135–158.

Davis, M. W., Somerville, D., Lee, R. Y., Lockery, S., Avery, L., and Fambrough, D. M. (1995). Mutations in the Caenorhabditis elegans Na,K-ATPase alpha-subunit gene, eat-6, disrupt excitable cell function, J Neurosci 15, 8408–18.

Dean, R. B. (1941). Theories of electrolyte equilibrium in muscle, Biological Symposia 3, 331–348.

El-Mallakh, R. S., and Wyatt, R. J. (1995). The Na,K-ATPase hypothesis for bipolar illness, Biol Psychiatry 37, 235–44.

Elkins, T., and Ganetzky, B. (1990). Conduction in the giant nerve fiber pathway in temperature-sensitive paralytic mutants of *Drosophila* , J Neurogenet 6, 207–219.

Elkins, T., B. Ganetzky and C. F. WU, 1986 A *Drosophila* mutation that eliminates a calcium-dependent potassium current. Proc Natl Acad Sci U S A 83: 8415–8419.

Feany, M. B., 2000 Studying human neurodegenerative diseases in flies and worms. J Neuropathol Exp Neurol 59: 847–856.

Feany, M. B., and W. W. Bender, 2000 A *Drosophila* model of Parkinson's disease. Nature 404: 394–398.

Feng, Y., Huynh, L., Takeyasu, K., and Fambrough, D. M. (1997). The *Drosophila* Na,K-ATPase alpha-subunit gene: gene structure, promoter function and analysis of a cold-sensitive recessive-lethal mutation, Genes Funct 1, 99–117.

Fletcher, C. F., C. M. Lutz, T. N. O'Sullivan, J. D. Shaughnessy, JR., R. Hawkes et al., 1996 Absence epilepsy in tottering mutant mice is associated with calcium channel defects. Cell 87: 607–617.

Forman, M. S., V. M. Lee and J. Q. Trojanowski, 2000 New insights into genetic and molecular mechanisms of brain degeneration in tauopathies. J Chem Neuroanat 20: 225–244.

Fortini, M. E., and N. M. Bonini, 2000 Modeling human neurodegenerative diseases in Drosophila : on a wing and a prayer. Trends Genet 16: 161–167.

Ganetzky, B., and Wu, C. F. (1982). Drosophila mutants with opposing effects on nerve excitability: genetic and spatial interactions in repetitive firing, J Neurophysiol 47, 501–14.

Geering, K. (1991). Posttranslational modifications and intracellular transport of sodium pumps: importance of subunit assembly, Soc Gen Physiol Ser 46, 31–43.

Goedert, M., 2001 The significance of tau and alpha-synuclein inclusions in neurodegenerative diseases. Curr Opin Genet Dev 11: 343–351.

Grinberg, A. V., Gevondyan, N. M., Grinberg, N. V., and Grinberg, V. Y. (2001). The thermal unfolding and domain structure of Na+/K+-exchanging ATPase. A scanning calorimetry study, Eur J Biochem 268, 5027–36.

Guennoun, S., and Horisberger, J. D. (2002). Cysteine-scanning mutagenesis study of the sixth transmembrane segment of the Na,K-ATPase alpha subunit, FEBS Lett 513, 277–81.

Hall, D. H., G. Gu, J. Garcia-Anoveros, L. Gong, M. Chalfie, et al., 1997 Neuropathology of degenerative cell death in Caenorhabditis elegans. J Neurosci 17: 1033–1045.

Hasler, U., Wang, X., Crambert, G., Beguin, P., Jaisser, F., Horisberger, J. D., and Geering, K. (1998). Role of beta-subunit domains in the assembly, stable expression, intracellular routing, and functional properties of Na,K-ATPase, J Biol Chem 273, 30826–35.

Heintz, N., and H. Y. Zoghbi, 2000 Insights from mouse models into the molecular basis of neurodegeneration. Annu Rev Physiol 62: 779–802.

Heisenberg, M. A. K. B., 1979 Isolation of anatomical brain mutants of Drosophila by histological means. Z. Naturforsch. 34c: 143–147.

Herrera, V. L., Chobanian, A. V., and Ruiz-Opazo, N. (1988). Isoform-specific modulation of Na+, K+-ATPase alpha-subunit gene expression in hypertension, Science 241, 221–3.

Hotta, Y., and Benzer, S. (1969). Abnormal electroretinograms in visual mutants of Drosophila , Nature 222, 354–356.

Jackson, G. R., I. Salecker, X. Dong, X. Yao, N. Arnheim et al., 1998 Polyglutamine-expanded human huntingtin transgenes induce degeneration of Drosophila photoreceptor neurons. Neuron 21: 633–642.

Jorgensen, P. L., Nielsen, J. M., Rasmussen, J. H., and Pedersen, P. A. (1998). Structure-function relationships of E1-E2 transitions and cation binding in Na,K-pump protein, Biochim Biophys Acta 1365, 65–70.

Kasbekar, D. P., Nelson, J. C., and Hall, L. M. (1987). Enhancer of seizure: a new genetic locus in Drosophila melanogaster defined by interactions with temperature-sensitive paralytic mutations, Genetics 116, 423–31.

Kazemi-Esfarjani, P., and S. Benzer, 2000 Genetic suppression of polyglutamine toxicity in Drosophila. Science 287: 1837–1840. Kretzschmar, D., G. Hasan, S. Sharma, M. Heisenberg and S. Benzer, 1997 The swiss cheese mutant causes glial hyperwrapping and brain degeneration in Drosophila. J Neurosci 17: 7425–7432.

Kuebler, D., Zhang, H., Ren, X., and Tanouye, M. A. (2001). Genetic suppression of seizure susceptibility in Drosophila , J Neurophysiol 86, 1211–1225.

Kuebler, D., and M. A. Tanouye, 2000 Modifications of seizure susceptibility in Drosophila. J Neurophysiol 83: 998–1009.

Lebovitz, R. M., Takeyasu, K., and Fambrough, D. M. (1989). Molecular characterization and expression of the (Na++K+)-ATPase alpha-subunit in Drosophila melanogaster, Embo J 8, 193–202.

Lees, G. J. (1993). Contributory mechanisms in the causation of neurodegenerative disorders, Neuroscience 54, 287–322.

Lees, G. J., and Leong, W. (1994). Brain lesions induced by specific and non-specific inhibitors of sodium-potassium ATPase, Brain Res 649, 225–33.

Leist, M., and P. Nicotera, 1998 Apoptosis, excitotoxicity, and neuropathology. Exp Cell Res 239: 183–201.

Lingrel, J. B., and Kuntzweiler, T. (1994). Na+,K(+)-ATPase, J Biol Chem 269, 19659–62.

Littleton, J. T., L. Pallanck and B. Ganetzky, 1999 Mechanisms of neurotransmitter release, pp. 139–161 in Int Rev Neurobiol 43, edited by V. Budnik and L. S. Gramates. Academic Press, San Diego.

Littleton, J. T., E. R. Chapman, R. Kreber, M. B. Garment, S. D. Carlson et al., 1998 Temperature-sensitive paralytic mutations demonstrate that synaptic exocytosis requires SNARE complex assembly and disassembly. Neuron 21: 401–413.

Loughney, K., R. Kreber and B. Ganetzky, 1989 Molecular analysis of the para locus, a sodium channel gene in Drosophila. Cell 58: 1143–1154.

Lutsenko, S., Anderko, R., and Kaplan, J. H. (1995). Membrane disposition of the M5-M6 hairpin of Na+,K(+)-ATPase alpha subunit is ligand dependent, Proc Natl Acad Sci U S A 92, 7936–40.

Lutsenko, S., and Kaplan, J. H. (1994). Molecular events in close proximity to the membrane associated with the binding of ligands to the Na,K-ATPase, J Biol Chem 269, 4555–64.

Maccioni, R. B., J. P. Munoz and L. Barbeito, 2001 The molecular bases of Alzheimer's disease and other neurodegenerative disorders. Arch Med Res 32: 367–381.

Magyar, J. P., Bartsch, U., Wang, Z. Q., Howells, N., Aguzzi, A., Wagner, E. F., and Schachner, M. (1994). Degeneration of neural cells in the central nervous system of mice deficient in the gene for the adhesion molecule on Glia, the beta 2 subunit of murine Na,K-ATPase, J Cell Biol 127, 835–45.

Min, K. T., and S. Benzer, 1997 Spongecake and eggroll: two hereditary diseases in Drosophila resemble patterns of human brain degeneration. Curr Biol 7: 885–888. Min, K. T., and S. Benzer, 1999 Preventing neurodegeneration in the Drosophila mutant bubblegum. Science 284: 1985–1988.

Mobasheri, A., Avila, J., Cozar-Castellano, I., Brownleader, M. D., Trevan, M., Francis, M. J., Lamb, J. F., and Martin-Vasallo, P. (2000). Na+, K+-ATPase isozyme diversity; comparative biochemistry and physiological implications of novel functional interactions, Biosci Rep 20, 51–91.

Molthagen, M., Schachner, M., and Bartsch, U. (1996). Apoptotic cell death of photoreceptor cells in mice deficient for the adhesion molecule on glia (AMOG, the beta 2-subunit of the Na, K-ATPase), J Neurocytol 25, 243–55.

Murtomaki, S., E. Trenkner, J. M. Wright, 0. Saksela and P. Liesi, 1995 Increased proteolytic activity of the granule neurons may contribute to neuronal death in the weaver mouse cerebellum. Dev Biol 168: 635–648.

Mutsuddi, M., and J. R. Nambu, 1998 Neural disease: *Drosophila* degenerates for a good cause. CurrBiol 8: R809–811.

Mynett-Johnson, L., Murphy, V., McCormack, J., Shields, D. C., Claffey, E., Manley, P., and McKeon, P. (1998). Evidence for an allelic association between bipolar disorder and a Na+, K+ adenosine triphosphatase alpha subunit gene (ATP1A3), Biol Psychiatry 44, 47–51.

Norman, D. J., L. Feng, S. S. Cheng, J. Gubbay, E. Chan et al., 1995 The lurcher gene induces apoptotic death in cerebellar Purkinje cells. Development 121: 1183–1193.

Pak, W. L., Grossfield, J., and White, N. V. (1969). Non-phototactic mutants in a study of vision of *Drosophila*, Nature 222, 351–354.

Palladino, M. J., Keegan, L. P., O'Connell, M. A., and Reenan, R. A. (2000). dADAR, a *Drosophila* double-stranded RNA-specific adenosine deaminase is highly developmentally regulated and is itself a target for RNA editing, RNA 6, 1004–1018.

Palladino, M. J., L. P. Keegan, M. A. O'Connell and R. A. Reenan (2000). A-to-I pre-mRNA editing in *Drosophila* is primarily involved in adult nervous system function and integrity. Cell 102: 437–449.

Pallanck, L., R. W. Ordway and B. Ganetzky, 1995 A *Drosophila* NSF mutant [letter]. Nature 376: 25.

Pavlidis, P., and Tanouye, M. A. (1995). Seizures and failures in the giant fiber pathway of *Drosophila* bang-sensitive paralytic mutants, J Neurosci 15, 5810–5819.

Renkawek, K., Renier, W. O., de Pont, J. J., Vogels, O. J., and Gabreels, F. J. (1992). Neonatal status convulsivus, spongiform encephalopathy, and low activity of Na+/K(+)-ATPase in the brain, Epilepsia 33, 58–64.

Sarvazyan, N. A., Modyanov, N. N., and Askari, A. (1995). Intersubunit and intrasubunit contact regions of Na+/K(+)-ATPase revealed by controlled proteolysis and chemical cross-linking, J Biol Chem 270, 26528–32.

Schubiger, M., Feng, Y., Fambrough, D. M., and Palka, J. (1994). A mutation of the *Drosophila* sodium pump alpha subunit gene results in bang-sensitive paralysis, Neuron 12, 373–81.

Shima, Y., Tada, Y., Furuki, M., Hara, Y., and Ohta, H. (1998). A missense mutation of the gene for Na+,K(+)-ATPase alpha-subunit causes abnormal feeding behavior in Caenorhabditis elegans, Biochem Biophys Res Commun 248, 778–82.

Sipione, S., and E. Cattaneo, 2001 Modeling huntington's disease in cells, flies, and mice. Mol Neurobiol 23: 21–51.

Skou, J. C. (1998). Nobel Lecture. The identification of the sodium pump, Biosci Rep 18, 155–69.

Sun, B., Wang, W., and Salvaterra, P. M. (1998). Functional analysis and tissue-specific expression of *Drosophila* Na+,K+-ATPase subunits, J Neurochem 71, 142–51.

Sun, B., Xu, P., Wang, W., and Salvaterra, P. M. (2001). In vivo modification of Na(+),K(+)-ATPase activity in *Drosophila*, Comp Biochem Physiol B Biochem Mol Biol 130, 521–36.

Swarts, H. G., Klaassen, C. H., de Boer, M., Fransen, J. A., and De Pont, J. J. (1996). Role of negatively charged residues in the fifth and sixth transmembrane domains of the catalytic subunit of gastric H+,K+-ATPase, J Biol Chem 271, 29764–72.

Taniguchi, K., Kaya, S., Abe, K., and Mardh, S. (2001). The oligomeric nature of Na/K-transport ATPase, J Biochem (Tokyo) 129, 335–42.

Therien, A. G., and Blostein, R. (2000). Mechanisms of sodium pump regulation, Am J Physiol Cell Physiol 279, C541–66.

Titus, S. A., Warmke, J. W., and Ganetzky, B. (1997). The *Drosophila* erg K+ channel polypeptide is encoded by the seizure locus, J Neurosci 17, 875–881.

Warrick, J. M., H. Y. Chan, G. L. Gray-Board, Y. Chai, H. L. Paulson et al., 1999 Suppression of polyglutamine-mediated neurodegeneration in *Drosophila* by the molecular chaperone HSP70. Nat Genet 23: 425–428.

Warrick, J. M., H. L. Paulson, G. L. Gray-Board, Q. T. Bui, K. H. Fischbeck et al., 1998 Expanded polyglutamine protein forms nuclear inclusions and causes neural degeneration in *Drosophila*. Cell 93: 939–949.

Wittmann, C. W., M. F. Wszolek, J. M. Shulman, P. M. Salvaterra, J. Lewis et al., 2001 Tauopathy in *Drosophila*: neurodegeneration without neurofibrillary tangles. Science 293: 711–714.

Wu, C. F., Ganetzky, B., Jan, L. Y., and Jan, Y. N. (1978). A *Drosophila* mutant with a temperature-sensitive block in nerve conduction, Proc Natl Acad Sci U S A 75, 4047–51.

Wu, C. F., and B. Ganetzky, 1992 Neurogenetic studies of ion channels in *Drosophila*, pp. 261–314 in Ion Channels 3, edited by T Narahashi. Plenum Press, New York.

Zuo, J., P. L. De Jager, K. A. Takahashi, W. Jiang, D. J. Linden et al., 1997 Neurodegeneration in Lurcher mice caused by mutation in delta2 glutamate receptor gene. Nature 388: 769–773.

---

We claim:

1. A method for evaluating a putative neuroprotective agent, the method comprising the steps of:

administering a putative neuroprotective agent to a *Drosophila* strain susceptible to age-dependent neurodegeneration, the strain being a behavioral mutant selected from the group consisting of a temperature-sensitive paralytic mutant and a bang-sensitive paralytic mutant; and evaluating a neuroprotective effect of the agent.

2. The method as claimed in claim 1 wherein a characteristic of the neuroprotective effect is selected from the group consisting of a reduction in severity of neurodegeneration, a delay in onset of neurodegeneration, an improved age-dependent behavior, and an increase in lifespan of the strain.

3. The method as claimed in claim 1 wherein the neuroprotective effect is evaluated by a histological screen.

4. The method as claimed in claim 1 wherein the agent is administered by a method selected from the group consisting of feeding the agent to the strain and injecting the agent into the strain.

* * * * *